(12) United States Patent
Wolf, II

(10) Patent No.: US 11,185,706 B2
(45) Date of Patent: Nov. 30, 2021

(54) APPARATUS AND METHOD FOR INCORPORATION OF OPTICAL SENSING INTO NEUROSTIMULATION SYSTEMS

(71) Applicant: Erich W. Wolf, II, Lake Charles, LA (US)

(72) Inventor: Erich W. Wolf, II, Lake Charles, LA (US)

(73) Assignee: WAVEGATE CORPORATON, Lake Charles, LA (US)

( * ) Notice: Subject to any disclaimer, the term of this patent is extended or adjusted under 35 U.S.C. 154(b) by 690 days.

(21) Appl. No.: 15/879,415

(22) Filed: Jan. 24, 2018

(65) Prior Publication Data

US 2018/0326219 A1     Nov. 15, 2018

Related U.S. Application Data

(60) Provisional application No. 62/449,933, filed on Jan. 24, 2017.

(51) Int. Cl.
| | |
|---|---|
| *A61N 1/375* | (2006.01) |
| *A61N 1/36* | (2006.01) |
| *A61N 1/05* | (2006.01) |
| *H05K 1/14* | (2006.01) |
| *G02B 7/00* | (2021.01) |
| *A61N 1/02* | (2006.01) |
| *A61N 1/372* | (2006.01) |
| *H05K 3/28* | (2006.01) |

(52) U.S. Cl.
CPC ......... *A61N 1/3758* (2013.01); *A61N 1/0551* (2013.01); *A61N 1/0553* (2013.01); *A61N 1/36071* (2013.01); *A61N 1/36171* (2013.01); *G02B 7/00* (2013.01); *H05K 1/144* (2013.01); *A61B 2562/0233* (2013.01); *A61N 1/025* (2013.01); *A61N 1/36139* (2013.01); *A61N 1/36175* (2013.01); *A61N 1/37229* (2013.01); *A61N 1/37264* (2013.01); *H05K 3/284* (2013.01)

(58) Field of Classification Search
CPC .. A61N 1/3758; A61N 1/0551; A61N 1/0553; A61N 1/36071
See application file for complete search history.

(56) References Cited

U.S. PATENT DOCUMENTS

| | | | |
|---|---|---|---|
| 6,011,993 A | 1/2000 | Tzviskos et al. | |
| 6,324,428 B1 | 11/2001 | Weinberg et al. | |
| 7,742,817 B2 | 6/2010 | Malinowski et al. | |
| 8,543,213 B2* | 9/2013 | Wolf, II | A61N 1/36139 607/46 |
| 9,132,273 B2* | 9/2015 | Wolf, II | A61N 1/3616 |
| 9,550,063 B2* | 1/2017 | Wolf, II | A61N 1/37264 |
| 9,656,097 B2* | 5/2017 | Wolf, II | A61N 1/3616 |
| 9,821,161 B2* | 11/2017 | Wolf, II | A61N 1/37264 |
| 10,035,019 B2* | 7/2018 | Wolf, II | A61N 1/37264 |
| 2009/0202202 A1 | 8/2009 | Lee et al. | |

(Continued)

*Primary Examiner* — Joseph M Dietrich
(74) *Attorney, Agent, or Firm* — Schultz & Associates, P.C.

(57) ABSTRACT

A connector system is provided for a positional sensitive spinal cord stimulation apparatus using near infrared reflectometry which incorporates the ability to connect to current IPG's either in a percutaneous or laminectomy form and which utilizes a novel light to frequency converter to generate a stimulation voltage in wave form to effect spinal cord stimulation.

51 Claims, 17 Drawing Sheets

(56) References Cited

U.S. PATENT DOCUMENTS

2013/0317573 A1\* 11/2013 Zhu .................... A61N 1/0529
607/89
2017/0252564 A1 9/2017 Wolf, II \* cited by examiner (PERCUTANEOUS LEAD)

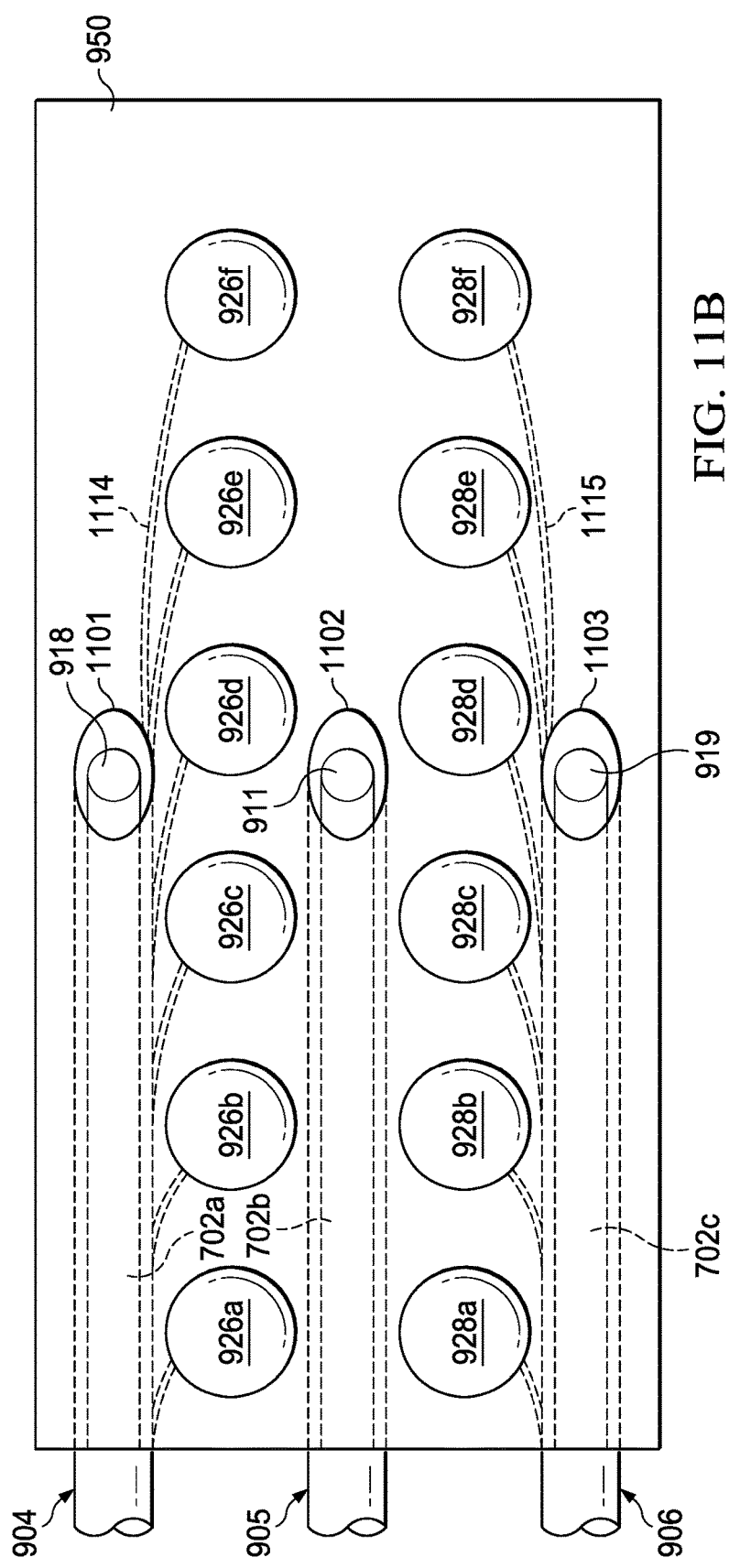
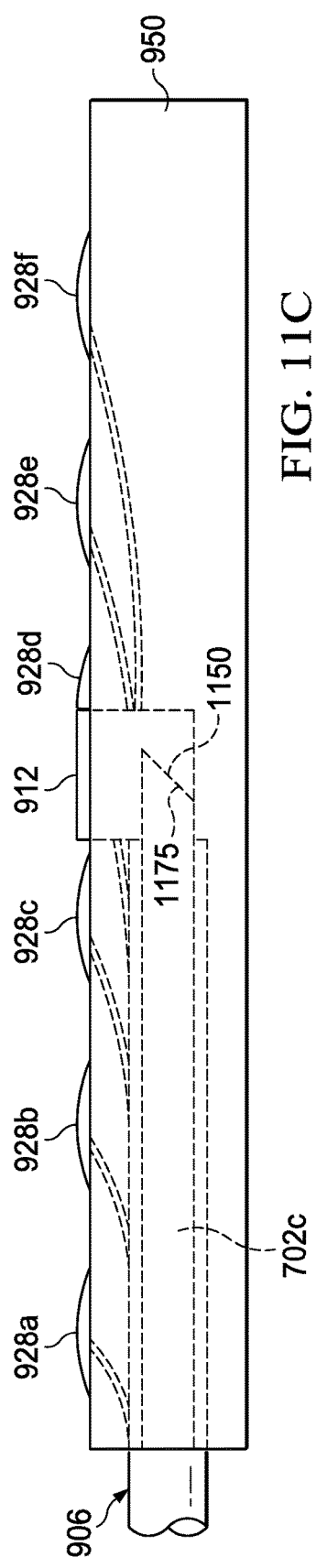
FIG. 11B
FIG. 11C

| Light Intensity A | Electrode Voltage/ Waveform $E_1$ | $E_2$ | $E_3$ | $E_4$ | $E_5$ | $E_6$ |
|---|---|---|---|---|---|---|
| 1 | $V_1/W_1$ | $V_2/W_2$ | $V_3/W_3$ | $V_4/W_4$ | $V_5/W_5$ | $V_6/W_6$ |
| 2 | $V_1/W_1$ | $V_2/W_2$ | $V_3/W_3$ | $V_4/W_4$ | $V_5/W_5$ | $V_6/W_6$ |
| 3 | $V_1/W_1$ | $V_2/W_2$ | $V_3/W_3$ | $V_4/W_4$ | $V_5/W_5$ | $V_6/W_6$ |
| 4 | $V_1/W_1$ | $V_2/W_2$ | $V_3/W_3$ | $V_4/W_4$ | $V_5/W_5$ | $V_6/W_6$ |
| 5 | $V_1/W_1$ | $V_2/W_2$ | $V_3/W_3$ | $V_4/W_4$ | $V_5/W_5$ | $V_6/W_6$ |
| 6 | $V_1/W_1$ | $V_2/W_2$ | $V_3/W_3$ | $V_4/W_4$ | $V_5/W_5$ | $V_6/W_6$ |
| 7 | $V_1/W_1$ | $V_2/W_2$ | $V_3/W_3$ | $V_4/W_4$ | $V_5/W_5$ | $V_6/W_6$ |
| 8 | $V_1/W_1$ | $V_2/W_2$ | $V_3/W_3$ | $V_4/W_4$ | $V_5/W_5$ | $V_6/W_6$ |
| 9 | $V_1/W_1$ | $V_2/W_2$ | $V_3/W_3$ | $V_4/W_4$ | $V_5/W_5$ | $V_6/W_6$ |
| 10 | $V_1/W_1$ | $V_2/W_2$ | $V_3/W_3$ | $V_4/W_4$ | $V_5/W_5$ | $V_6/W_6$ |

FIG. 15

APPARATUS AND METHOD FOR INCORPORATION OF OPTICAL SENSING INTO NEUROSTIMULATION SYSTEMS

CROSS-REFERENCE TO RELATED APPLICATIONS

This application claims priority to U.S. Provisional Patent Application No. 62/449,933, filed Jan. 24, 2017. Each patent application identified above is incorporated here by reference in its entirety to provide continuity of disclosure.

FIELD OF DISCLOSURE

This disclosure relates generally to spinal cord stimulation (SCS) and technique for automatic adjustments of SCS using near-infrared (NIR) reflectometry.

BACKGROUND

Chronic pain may arise from a variety of conditions, most notably from nerve injury as in the case of neuropathic pain, or from chronic stimulation of mechanical nociceptors such as with spinal pain. Functional ability may be severely impacted by pain, which often is refractory to pharmacological and surgical treatment. In such cases, spinal cord stimulation ("SCS") can be an effective treatment for pain by modulating physiological transmission of pain signals from the periphery to the brain. This may be achieved by applying electrical impulses to the spinal cord via an electrode array placed in the dorsal epidural space.

In FIG. 1, spinal column 100 is shown to have a number of vertebrae, categorized into four sections or types: lumbar vertebrae 102, thoracic vertebrae 104, cervical vertebrae 106 and sacral vertebrae 108. Cervical vertebrae 106 include the 1st cervical vertebra (C1) through the 7th cervical vertebra (C7). Just below the 7th cervical vertebra is the first of twelve thoracic vertebrae 104 including the 1st thoracic vertebra (T1) through the 12th thoracic vertebra (T12). Just below the 12th thoracic vertebrae 104, are five lumbar vertebrae 102 including the 1st lumbar vertebra (L1) through the 5th lumbar vertebra (L5), the 5th lumbar vertebra being attached to sacral vertebrae 108 (S1 to S5), sacral vertebrae 108 being naturally fused together in the adult. Electrical lead 110 is implanted between thoracic vertebrae 104, such that electrical lead 110 may deliver an electric current to spinal root nerves. Electrical lead 110 is attached via lead wire 112 to implantable pulse generator ("IPG") 116. IPG 116 has a header 114 that allows lead wire 112 to attach, but can be removed to allow IPG 116 to be replaced or serviced without disturbing electrical lead 110.

Referring to FIG. 2, alternate electrical leads 200 are shown. Percutaneous lead 202 includes optical fiber 204, optical element 206, electrodes 208 and contacts 210. Optical fiber 204 is coupled to optical element 206. Percutaneous lead 202 also includes electrical wires. Percutaneous lead 214 is of similar construction having optical element 218, electrodes 220, contacts 222 and optical fiber 216. The optical fibers are used to transmit light signals to be used near infrared position detection of the spinal cord, as known in the art.

Referring to FIG. 3, a cross-sectional view of vertebra 300 is shown enclosing spinal cord 302. Percutaneous lead 304 and percutaneous lead 306 are implanted in epidural space 308 of vertebra 300 between dura 310 and the walls of the spinal canal 312. In a preferred embodiment, the percutaneous leads are implanted side-by-side at a predetermined distance apart, adjacent, and generally parallel to, each other. Placement of percutaneous leads 304 and 306 can be accomplished through insertion of the leads through needles placed percutaneously into the epidural space.

Referring to FIG. 4A, a surgical lead is shown. Surgical lead 400 includes an elastomeric housing 401 connected to lead 410 and to lead 411. Embedded in elastomeric housing 401, are optical fiber 402, optical fiber 403, electrodes 412 and electrodes 413. Optical fiber 402 is terminated with optical element 408. Optical fiber 403 is terminated with optical element 409. Lead 410 encloses optical fiber 402 and wires 404 which are terminated in opto-electrical connector 406. Lead 411 encloses optical fiber 403 and wires 405 which are terminated in opto-electrical connector 407. The fibers are used to accommodate near infrared reflectometry.

Referring to FIG. 4B, thoracic vertebra 450 is shown. The thick oval segment of bone forming the anterior aspect of vertebra 450 is vertebral body 452. Vertebral body 452 is attached to bony vertebral arch 454 through which spinal nerves 456 run. Vertebral arch 454, forming the posterior of vertebra 450, is comprised of two pedicles 458, which are short stout processes that extend from the sides of vertebral body 452 and bilateral laminae 460. The broad flat plates that project from pedicles 458 join in a triangle to form a hollow archway, spinal canal 462. Spinous process 464 protrudes from the junction of bilateral laminae 460. Transverse processes 466 project from the junction of pedicles 458 and bilateral laminae 460. The structures of the vertebral arch protect spinal cord 468 and spinal nerves 456 that run through the spinal canal.

Surrounding spinal cord 468 is dura 470 that contains cerebrospinal fluid (CSF) 472. Epidural space 474 is the space within the spinal canal lying outside the dura.

An IPG delivers pulses of electrical current to the electrode array, which stimulates targeted neurons within the ascending tracts of the spinal cord and disrupts the perception of pain. Controlling the amplitude of the stimulating electrical current is paramount to success of spinal cord stimulation. Applying inadequate current will fail to depolarize the targeted neurons, rendering the treatment ineffective. Conversely, application of too strong a current will depolarize the targeted neurons, but also stimulate additional cell populations which renders the perception of a noxious stimulation.

Establishing a consistent, therapeutic, and non-noxious level of stimulation is predicated upon establishing an ideal current density within the spinal cord's targeted neurons. Fundamentally, this should be a simple matter of establishing an optimal electrode current given the local bulk conductivity of the surrounding tissues. Unfortunately, in practice, the optimal electrode current changes as a function of patient position and activity due to motion of the spinal cord as the spinal cord floats in cerebrospinal fluid within the spinal canal. Significant changes in distance between the epidural electrode array and the targeted spinal cord neurons have been shown to occur. Consequently, it is preferred to dynamically adjust the electrode stimulating current as a function of distance between the electrode array and the spinal cord.

Dynamic modulation of spinal cord stimulator electrode current as a function of distance between the electrode array and the spinal cord thus has several benefits. Too high a stimulation current can be avoided, thus reducing the prospects of noxious stimulation and potentially reducing device power consumption. Too low a stimulation current can be avoided, thus eliminating periods of inadequate stimulation and compromised therapeutic efficacy.

A patient who is a candidate for treatment first undergoes a trial period whereby electrical leads are implanted percutaneously. The leads are connected to an IPG that is worn outside the body. Percutaneous leads connected to an external pulse generator provide certain advantages that make them useful for trial periods, because they can be installed without the need for major surgery. However, having the leads connected to an external IPG presents risks from potential injury or infection. Hence, for patients requiring long-term treatment, the IPG is connected to the leads subcutaneously and permanently implanted.

The IPG is typically implanted near the upper buttocks or flank. The IPG is intended to remain in a single orientation after implantation, and therefore must be fitted into a pocket of tissue that is no larger than necessary. Both the incision and pocket created must therefore match dimensions of the IPG used. An improper fit risks movement of the IPG, which could impede charging or tangle the electrode leads.

One challenge to IPG treatment is that the percutaneous leads are susceptible to movement over time. As the leads move, the distance to the spinal cord segment changes, requiring a new level of electrical current to maintain the efficacy of treatment. One way of addressing this challenge is through the use of near infrared reflectometry. An optical signal can be transmitted into the surrounding tissue, and collected by a sensor to calculate the approximate distance between the electrode and the target nerve. An example of this technology is shown in U.S. Publication No. 2017/0252564, now U.S. Pat. No. 10,035,019 to Wolf.

Another challenge to IPG treatment is the long-term survival of the electrode array and optoelectronics in the harsh in vivo environment. Functional and mechanical degradation may occur with the ingress of body fluids. Proteins common in the blood and interstitial fluid are known to bind to metallic ions, leading to corrosion. Some materials can trigger an immune response and potentially a change in the local pH balance of the implantation site. Specialized polymers and epoxies can avoid some of these problems, but often exhibit unacceptably high levels of cytotoxicity. Moreover, electronic devices implanted in the body must be sealed, because bodily fluids contain a great number of ions, such as sodium ions, that are not electrically inert.

Hermetic sealing of electronics is generally required for long-term sustainability. Current manufacturing techniques generally utilize potting of electronics within a biocompatible epoxy. Epoxies are desirable materials to achieve biocompatibility, but do not provide a lasting hermetic seal. Epoxies can leak, allowing bodily fluids to penetrate into the implant, at a rate of between $10^5$ and $10^6$ cubic centimeters of fluid per second. At such a rate, epoxy-coated implants will typically have a viability of no more than 15-20 years after implantation. Proper potting can achieve reliability upward of ten years, which is commensurate with the expected IPG battery life but falls short of the service life of an electrode array.

Another challenge to implementation of NIR-reflectometry for adaptive spinal cord stimulation has been the requirement to change the IPG to incorporate the necessary optoelectronic devices. Such a change would require a significant engineering endeavor, increased tooling and manufacturing costs, and overcoming considerable regulatory hurdles.

Another challenge of implementation of NIR-reflectometry is the need for repeated surgery. Components that must be very near the spinal cord, such as subcutaneous leads or optical sensors, are difficult to access after implantation, and should not be designed to require regular adjustment or maintenance because such would require repeated spinal surgery. The number and risk level of the later surgeries required to maintain the IPG systems should be minimized. Currently, batteries in IPGs must be replaced approximately once every 3-7 years. However, optoelectronics are anticipated to require replacement approximately once every 7-10 years. Doing so typically requires surgery on the spine itself, as the optics must be placed near the targeted spinal cord segment. The entire system must be replaced every 15-20 years.

The prior art has attempted to address these challenges in a number of ways.

For example, U.S. Pat. No. 6,011,993 to Tziviskos, et al. describes a method of making a strong ceramic case that can house electronics with a good hermetic seal for implantation into the body. However, the patent does not describe how to effectively connect electrical leads or optical fibers, nor does it describe a system for replacing a failing battery.

U.S. Pat. No. 6,324,428 to Weinberg, et al. describes a design for a medical implant that contains the internal electronics in a preferred configuration that minimizes the volume of the implant, making it easier to implant. However, the patent does not describe any designs that could alleviate the need for, or degree of risk involved in, follow up surgeries after implantation.

Similarly, U.S. Pat. No. 7,742,817 to Malinowski, et al. describes an IPG with connectors for electrical leads and an epoxy coating for biocompatibility. However, the patent does not disclose the use of optics in the design to achieve proper pulse strength.

Thus, there is a need in the art for a connector which attaches to an existing IPG without significant reengineering. There is also a need for placement of optoelectronics in a position to minimize the effects of biodegradation and repeated high risk surgery.

SUMMARY

To achieve the requirements for indefinite life-time of the electrode array and requiring no physical changes to the IPG, while allowing for IPG battery changes at up to 10 year intervals, the optoelectronics may be housed in a hermetically-sealed connector which is easily accessed and changed at the time of IPG replacement. The connector acts as an interface between the leads that connect to the electrode array and the IPG. The connector consists, generally, of a body having ports which accommodate electrode leads, and flexible leads which accommodate the IPG header. The electrode leads incorporate optical fiber assemblies which convey light either to or from the lead tip to the optoelectronics which are housed in the connector. The leads are inserted into the connector. The connector is then connected to the IPG header. Two electrode contacts from each of two leads are repurposed to serve the optoelectronics in the connector. The connector leads are kept short so that the connector may be "tucked" behind the IPG during implantation so that it may be changed easily when the IPG is replaced. Existing IPGs generally have 16, 24, or 32 channels of which four or fewer would be repurposed for operation of the optoelectronics. Placement of the optoelectronics in the connector assures that the optoelectronics will be replaced at intervals less than the anticipated lifetime of the hermetic potting.

BRIEF DESCRIPTION OF DRAWINGS

The following disclosure is understood best in association with the accompanying figures. Like components share like numbers.

FIG. 11B is a plan view of a paddle shaped laminectomy lead of a preferred embodiment of a laminectomy lead contact.

FIG. 11C is a side view of a preferred embodiment of the paddle shaped laminectomy lead of the laminectomy lead contact.

FIG. 15 is a preferred embodiment of a look-up table for light intensity versus electrode voltage and wave form.

DETAILED DESCRIPTION

Figure 1:
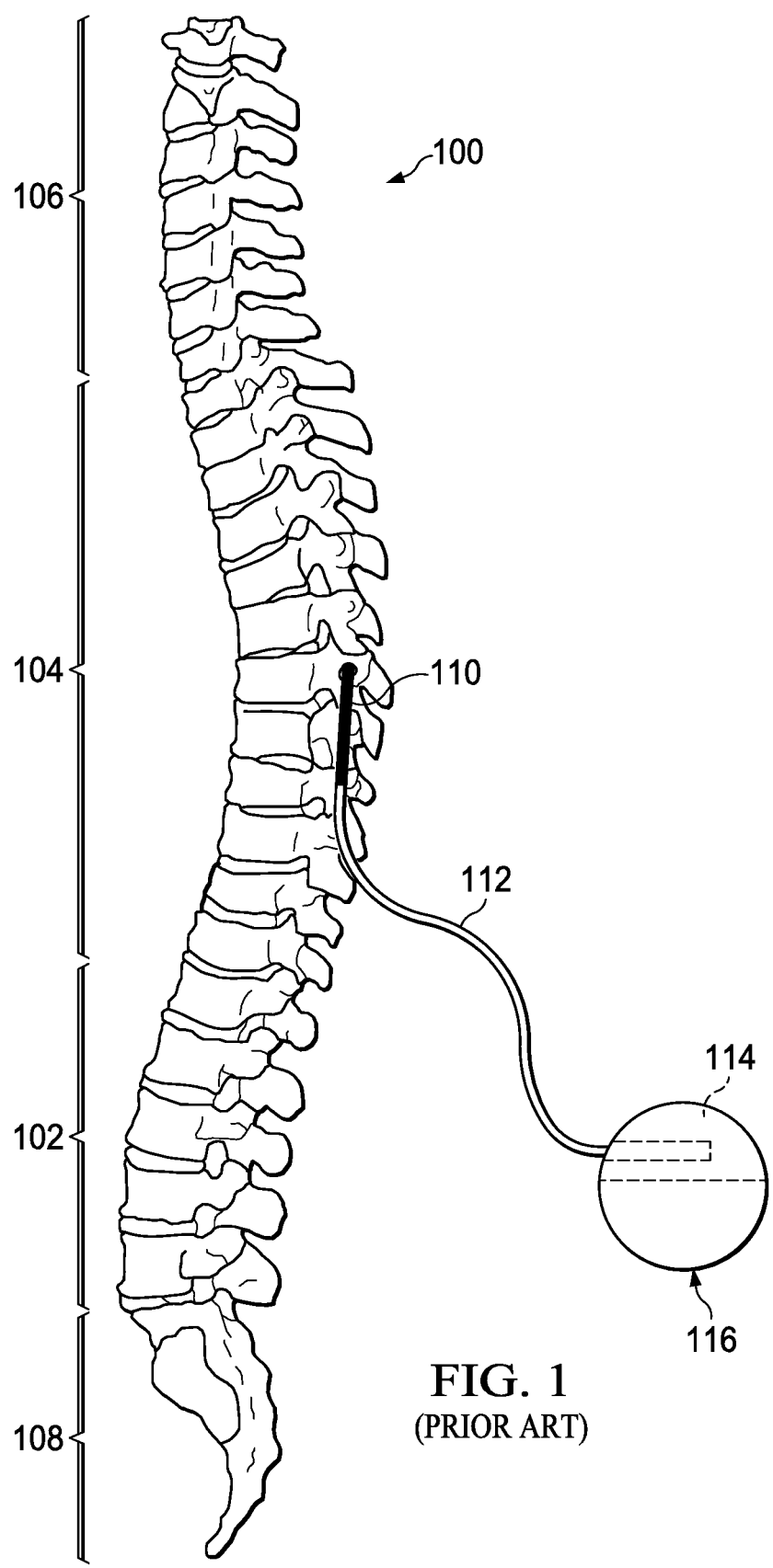
FIG. 1 shows a view of the human spine showing the various types of vertebrae and an approximate position of an electrode array for spinal cord stimulation.
Figure 2:
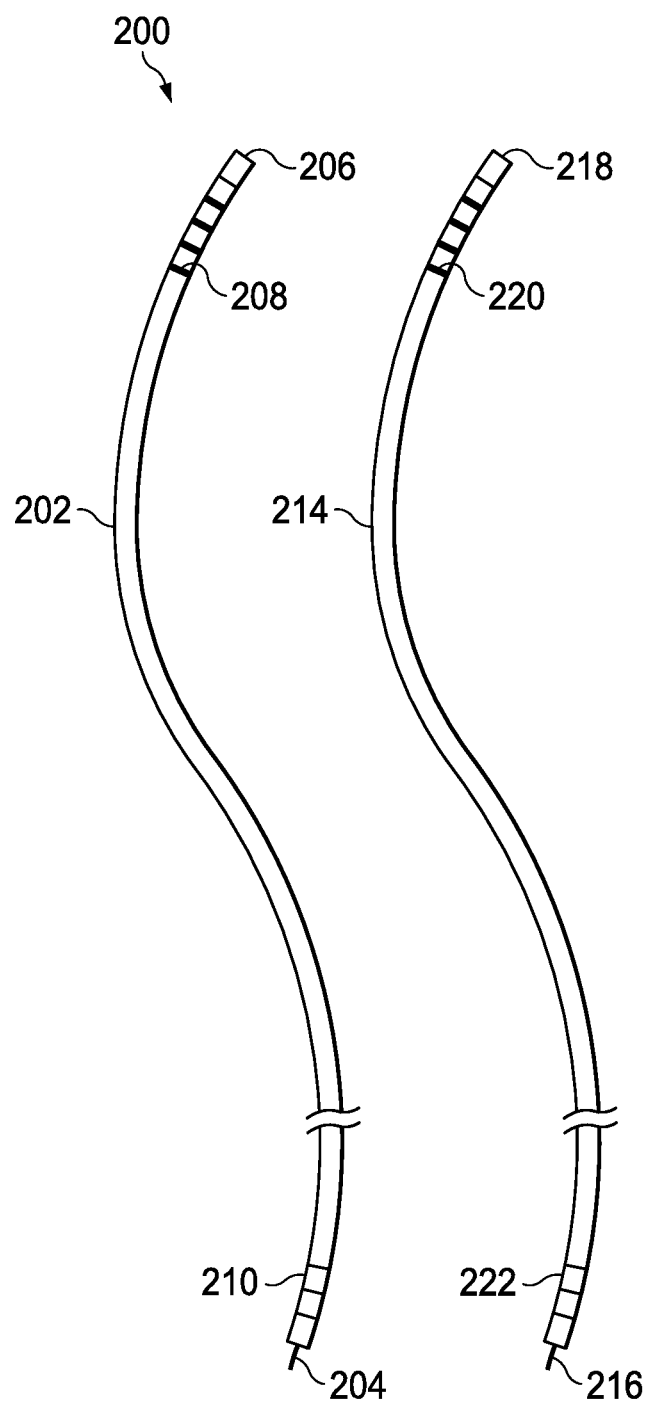
FIG. 2 shows a perspective view of a preferred embodiment of a paired percutaneous lead.
Figure 3:
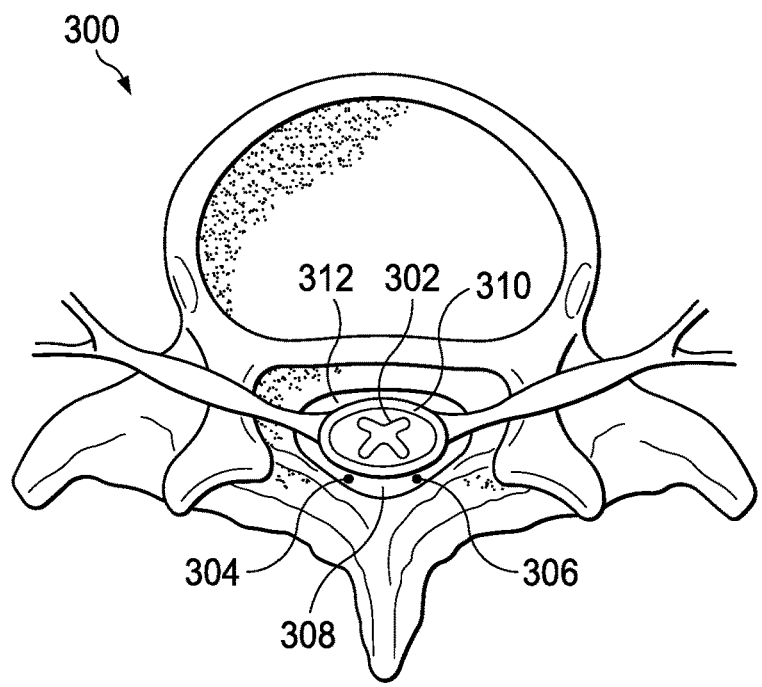
FIG. 3 shows preferred placement of a paired percutaneous surgical lead in a spinal column.
Figure 4B:
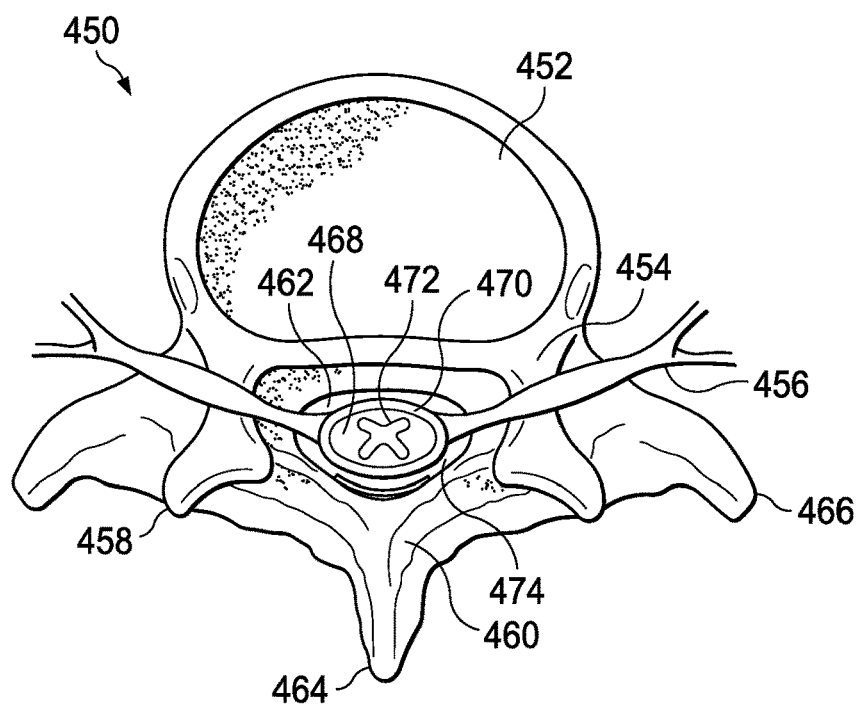
FIG. 4B shows an axial view of a thoracic vertebra indicating the position of the spinal cord and an electrode array for spinal cord stimulation.
Figure 4A:
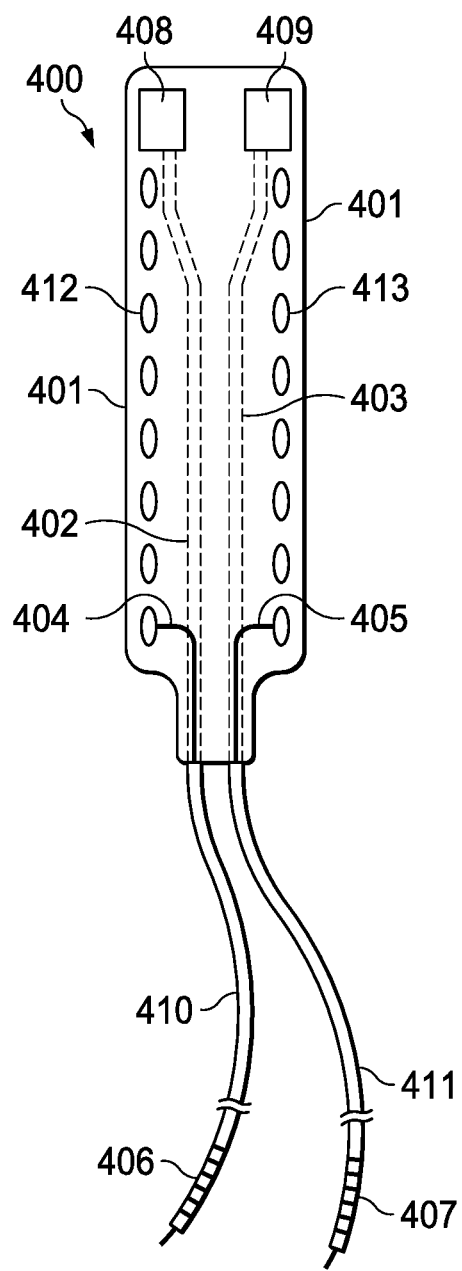
FIG. 4A shows a preferred embodiment of a surgical lead.
Figure 5:
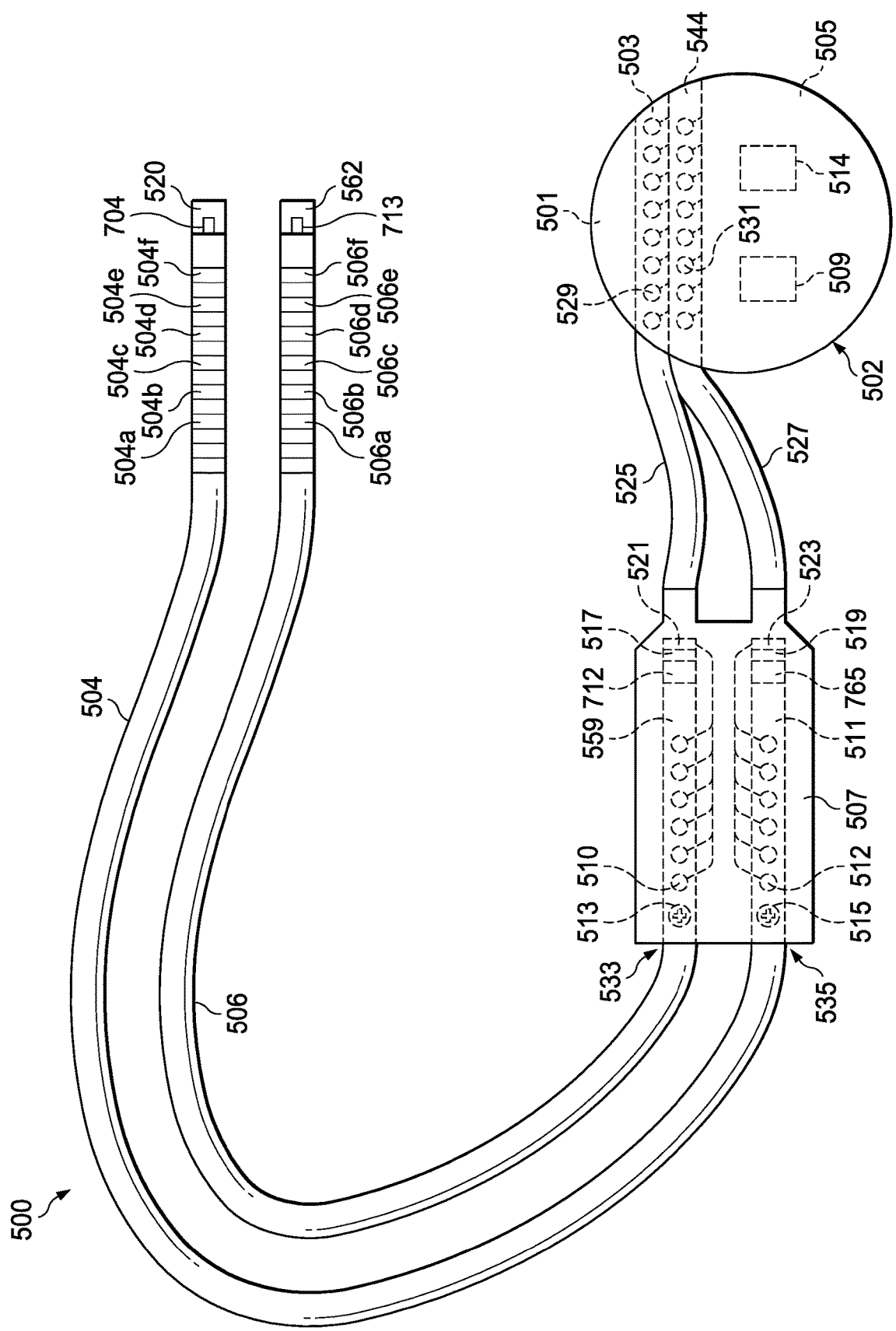
FIG. 5 is a system drawing of a preferred embodiment of the percutaneous lead connector system.

Turning then to FIG. 5, percutaneous connector system 500 includes IPG 502 connected to percutaneous lead connector 507 by flexible leads 525 and 527. Percutaneous lead connector 507 is in turn connected to flexible leads 504 and 506.

IPG 502 further includes IPG body 505. In a preferred embodiment, IPG body 505 is a stainless steel container capable of being hermetically sealed. IPG body 505 houses battery 509 operatively connected to processor 514. The processor is preferably a MSP430 microprocessor available from Texas Instruments. IPG 502 further includes connector arrays 503 and 544 included in header 501. In a preferred embodiment, header 501 is hermetically sealed to IPG body 505. In a preferred embodiment, IPG 502 is a commercially available spinal cord stimulator generator (IPG). Connector array 503 includes contacts 529. Connector array 554 includes contacts 531. In this embodiment, the IPG provides eight contacts in each connector array. Two of the connectors in each array are used to transmit control voltages to and from LEDs and optical sensors, as will be further described.

Percutaneous lead connector 507 includes connector array 559 and connector array 511. In a preferred embodiment, the connector body can be formed of poly (methyl methacrylate), polyvinyl chloride, a flexible Silastic elastomer, or a suitable epoxy resin. Connector array 559 includes contacts 510. Connector array 511 includes contacts 512. As will be further described, contacts 510 are connected to contacts 529 through flexible lead 525. As will be further described, contacts 512 are connected to contacts 531 through flexible lead 527.

Percutaneous lead connector 507 further comprises cylindrical port 533 and cylindrical port 535. Cylindrical port 533 accommodates flexible lead 507. Cylindrical port 535 accommodates flexible lead 504. Flexible lead 504 includes electrodes 504a-504f and transparent tip 520, as will be further described. Flexible lead 506 includes electrodes 506a-506f and transparent tip 562, as will be further described. In a preferred embodiment, wires (not shown) are encapsulated in flexible lead 504 and individually connect electrodes 504a-504f to contacts 512. Likewise, wires (not shown) are encapsulated in flexible lead 506 and individually connect electrodes 506a-506f to contacts 510.

Cylindrical port 533 houses lens array 517 and LED 521, as will be further described. Likewise, cylindrical port 535 houses lens array 519 and light to frequency converter (LFC) 523, as will be further described.

Transparent tip 520 is optically connected by an internal fiber optic cable, to lens array 519. Likewise, transparent tip 562 is optically connected by an internal fiber optic cable to lens array 517.

Figure 6A:
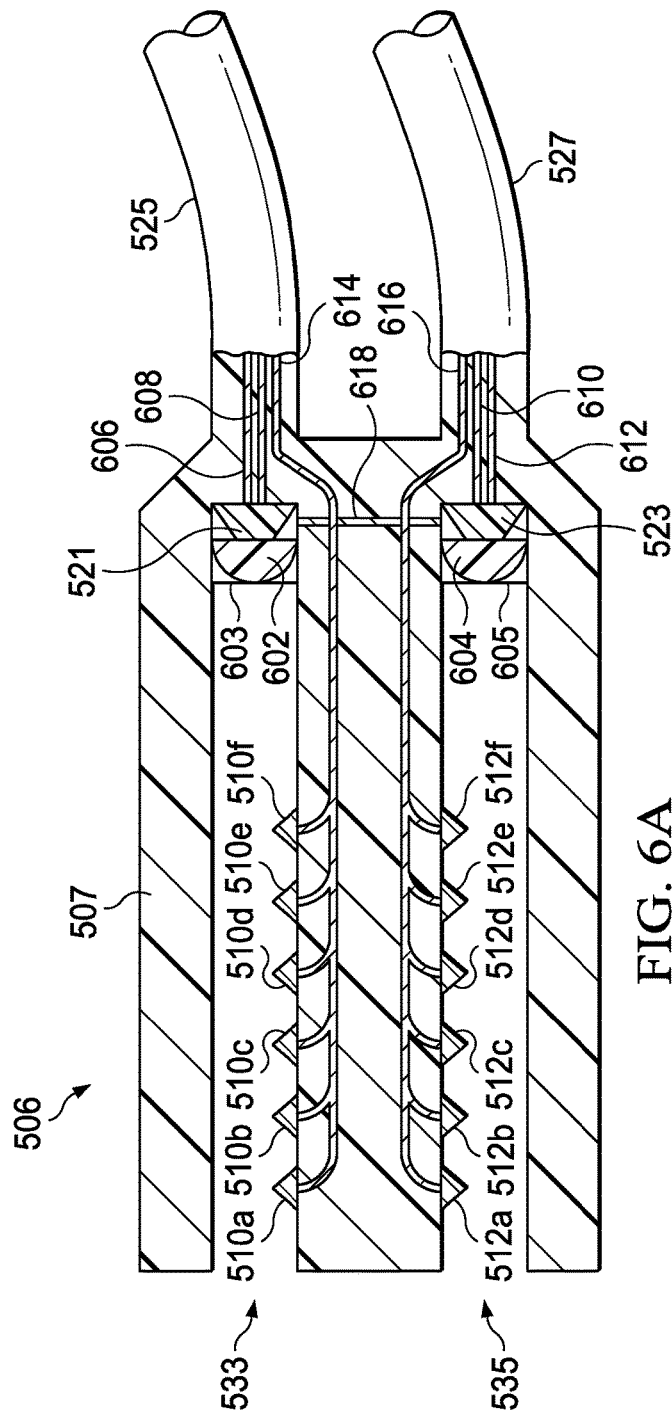
FIG. 6A is a cross sectional drawing of a preferred embodiment of the percutaneous lead connector.

Turning then to FIG. 6A, percutaneous lead connector 507 will be further described. Cylindrical port 533 is typically 1.5 millimeters in diameter (±10%). Similarly, cylindrical port 535 is typically 1.5 millimeters in diameter (±10%). Lens array 517 is rigidly fixed at the proximal end of cylindrical port 533 by a suitable epoxy. Lens array 517 further comprises coupling surface 603 and lens 602. In a preferred embodiment, lens 602 is encased in poly (methyl methacrylate). The encasement forms coupling surface 603, which is optically polished. In a similar way, lens array 519 is rigidly fixed at the proximal end of cylindrical port 535. Lens 604, in a preferred embodiment, is encased in poly (methyl methacrylate), which is optically polished to form coupling surface 605. Lens 602 and lens 604, in a preferred embodiment, are collimating lenses designed to reduce light loss. LED 521 is positioned adjacent lens 602 at the proximal end of cylindrical port 533. In a preferred embodiment, LED 521 is a high-speed, infrared emitting diode of 850 nanometers wavelength and available as part no. 1850VSMY available from Vishay Intertechnology, Inc. of Malvern, Pa.

LFC 523 is positioned adjacent lens 604 and held in place by a suitable epoxy at the proximal end of cylindrical port 535. In a preferred embodiment LFC 523 is part no. TSL 238T high-sensitivity light to frequency converter available from Texas Advanced Optoelectronic Solutions of Plano, Tex. Using a digital detector obviates the requirements for analog-to-digital conversion which speeds processing time and conserves battery power. It also eliminates concerns over leakage currents affecting measurement accuracy, thereby increasing sustained accuracy and reducing calibration time and overhead. Flexible lead 525 includes eight wires which are, LED line 606, ground line 608, and electrode line bundle 614. Electrode line bundle 614 includes six individual wires. In a preferred embodiment, each of the wires in the electrode line bundles are comprised of a relatively inert nichrome. Flexible lead 527 includes eight wires, electrode line bundle 616, data line 610 and VCC line 612. Electrode line bundle 616 includes six individual wires. LED 521 is connected to LFC 523 by bridge connection 618, as will be further described. Bridge connection 618 supplies VCC and ground.

Figure 6B:
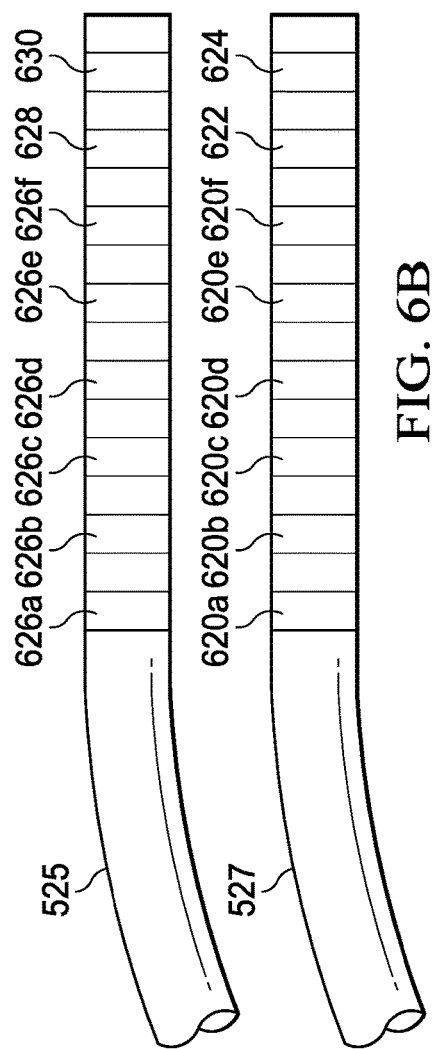
FIG. 6B is a preferred embodiment of the flexible leads of the percutaneous lead connector.

Turning then to FIG. 6B, flexible lead 525 includes electrodes 626a-626f, 628 and 630. Each of electrodes 626a-626f is connected to a separate single wire in electrode line bundle 614. In a preferred embodiment, LED line 606 is connected to electrode 628. In a preferred embodiment, ground line 608 is connected to electrode 630. In this way, each of the electrodes is separately addressable.

Flexible lead 527 includes electrodes 620a-620f, 622 and 624. In a preferred embodiment, data line 610 is connected to electrode 622. In a preferred embodiment, VCC line 612 is connected to electrode 624. Likewise, each of electrodes 620a-620f is connected to a separate single wire in electrode line bundle 616. In this way, each of the electrodes is separately addressable.

Cylindrical port 533 further includes integrally formed contacts 510a-510f. Each of integrally formed contacts 510a-510f is individually connected to one wire in electrode line bundle 614. Cylindrical port 535 includes integrally formed contacts 512a-512f. Each of integrally formed contacts 512a-512f is connected to an individual wire in electrode line bundle 616. In a preferred embodiment, each of integrally formed contacts 510a-510f and 512a-512f are conically formed and embedded in an interior surface of cylindrical ports 533 and 535, respectively. In a preferred embodiment, each of the integrally formed contacts is a raised conical shape, formed of a gold or a platinum alloy.

Figure 7A:
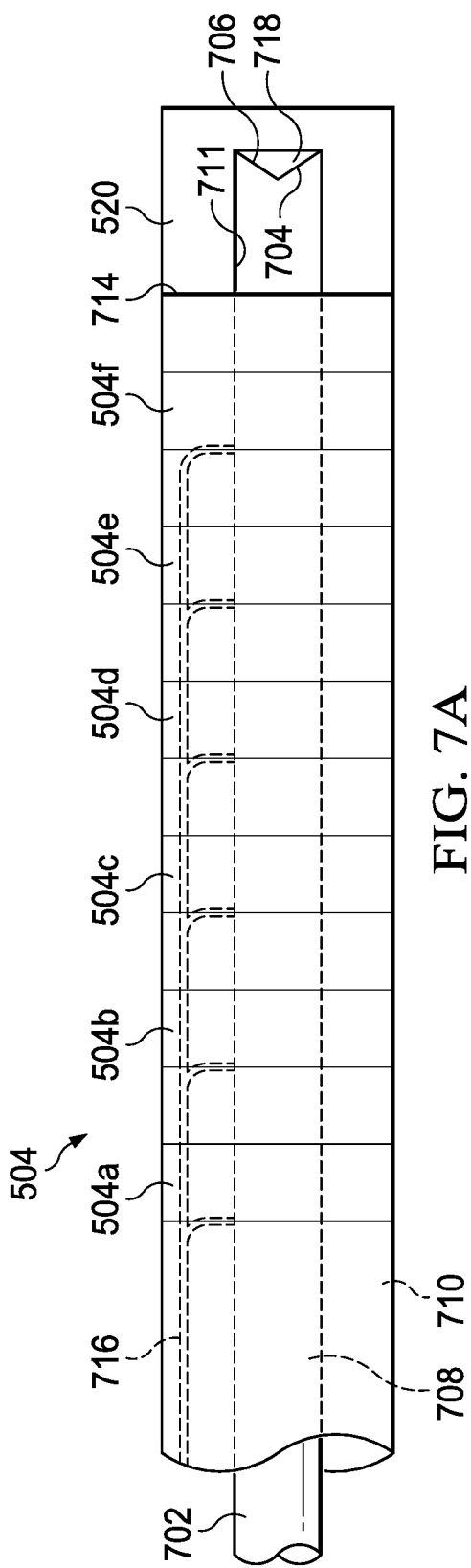
FIGS. 7A and 7B are drawings of a preferred embodiment of a flexible lead of the percutaneous lead connector.
Figure 7B:
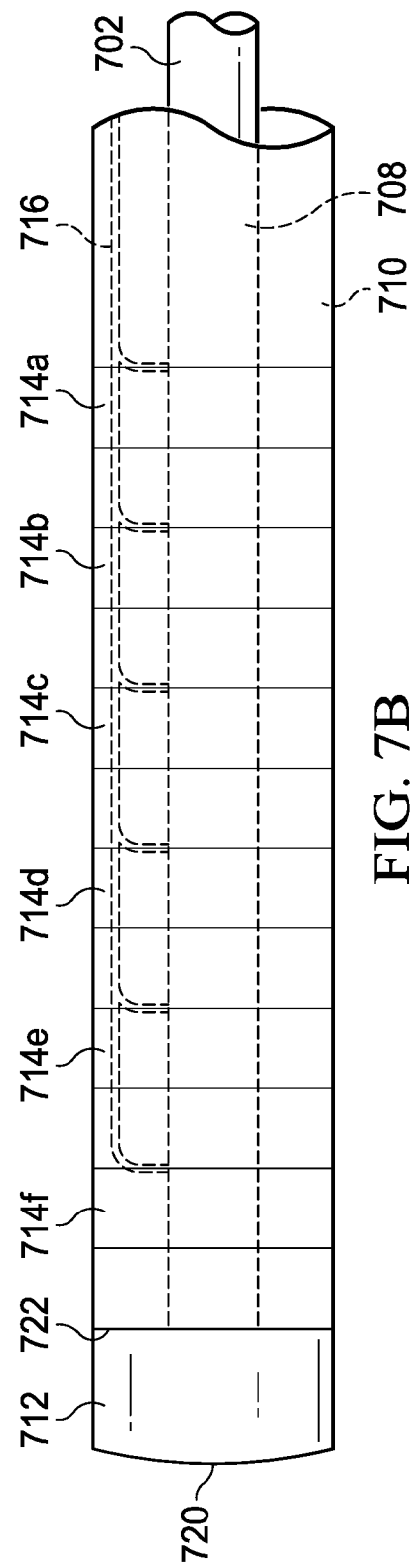

Moving then to FIGS. 7A and 7B, flexible lead 504 will be further described. Flexible lead 504 further comprises lead body 710. Lead body 710, in a preferred embodiment, is comprised of a biologically inert polymer such as pellathane-55D. The flexible lead is typically about 60 cm long and has a diameter of about 1.5 mm.

Cylindrical contacts 714a-714f are embedded within lead body 710 at regular intervals. In a preferred embodiment, each of the electrodes is coaxial and comprised of platinum or platinum alloy and is positioned along the proximal end of flexible lead 504. The distal end of lead body 710 further comprises electrodes 504a-504f. Electrodes 504a-504f are cylindrical and coaxial, and in a preferred embodiment, are comprised of a platinum or a platinum alloy. Electrodes 504a-504f are spaced at regular intervals on the exterior surface of the lead body and, when assembled with percutaneous lead connector 507, form an electrical contact with each of integrally formed contacts 512a-512f. In a preferred embodiment, electrode 504a, is connected to integrally formed contact 512a. In a preferred embodiment, electrode 504b, is connected to integrally formed contact 512b. In a preferred embodiment, electrode 504c, is connected to integrally formed contact 512c. In a preferred embodiment, electrode 504d, is connected to integrally formed contact 512d. In a preferred embodiment, electrode 504e, is connected to integrally formed contact 512e. In a preferred embodiment, electrode 504f, is connected to integrally formed contact 512f.

In a preferred embodiment, electrode 504a is connected to an individual wire in electrode line bundle 716, which is, in turn, connected to cylindrical contact 714a. Electrode 504b is connected to an individual wire in electrode line bundle 716, which is, in turn, connected to cylindrical contact 714b. Electrode 504c is connected to an individual wire in electrode line bundle 716, which is, in turn, connected to cylindrical contact 714c. Electrode 504d is connected to an individual wire in electrode line bundle 716, which is, in turn, connected to cylindrical contact 714d. Electrode 504e is connected to an individual wire in electrode line bundle 716, which is, in turn, connected to cylindrical contact 714e. Electrode 504f is connected to an individual wire in electrode line bundle 716, which is, in turn, connected to cylindrical contact 714f.

Electrode line bundle 716 is formed integrally with lead body 710 and is isolated from contact with bodily fluids. Transparent tip 520 is located at the distal end of flexible lead 504. Transparent tip 520 is cylindrical and is attached to lead body 710 at interface 714 with a suitable epoxy adhesive. In a preferred embodiment, transparent tip 520 is comprised of poly (methyl methacrylate) and is optically transparent. Transparent tip 520 includes optical cavity 711. In a preferred embodiment, optical cavity 711 is cylindrical and is of an appropriate diameter to accommodate optical fiber assembly 702. In another preferred embodiment, the optical fiber assembly is allowed to float within the lead body. Binding of the optical fiber or the transparent tip to the lead body or electrodes is prevented by providing a gap at interface 714 of about 1/16".

Lead body 710 further comprises central lumen 708. The central lumen is typically used for positioning of the lead during surgery. However, after implantation the lumen is left open. Removably disposed within central lumen 708 is optical fiber assembly 702. The optical fiber composition is preferably a poly (methyl methacrylate), a biocompatible acrylic or a borosilicate glass. The cladding of the fiber is preferably a fluorinated polymer such as polytetrafluoroethylene or polyvinyl chloride. The optical fiber assembly may be inserted into the central lumen after implantation of the flexible lead or formed internally with the flexible lead at the time of manufacture. Optical fiber assembly 702 includes integrally formed collet 712 at its proximal end. Collet 712 is cylindrical and has a diameter approximately equal to that of lead body 710. Collet 712 includes polished optical surface 720. Polished optical surface includes a radius, which forms a collimating lens for efficient transfer of light. In a preferred embodiment, polished optical surface 720 is integrally formed with optical fiber assembly 702. In another preferred embodiment, collet 712 is separately machined from an optical glass and attached to optical fiber assembly 702 at interface 722. Optical fiber assembly 702 includes negative axicon 704 at its distal end. Negative axicon 704 includes a 45° inverted cone arrangement and produces a radial reflection perpendicular to the longitudinal axis of the lead.

Negative axicon 704 includes $TiO_2$ nanoparticle surface cladding 706 on its internal surface. Negative axicon 704 further includes backfill 718. In a preferred embodiment backfill 718 is comprised of a suitable epoxy, which binds the $TiO_2$ nanoparticle surface cladding to the interior surface of the negative axicon. Alternatively, the $TiO_2$ nanoparticles may be mixed into the backfill before application. In a preferred embodiment, the epoxy is Epotek 302. The $TiO_2$ nanoparticle surface cladding is important because it increases the amount of light reflected into or out of the optical fiber assembly.

Flexible lead 506 is of the same construction and has all similar components as flexible lead 504 and connects electrodes 507a-507f to integrally formed contacts 510a-510f, respectively, via an electrode line bundle, and physically positions collet 765 adjacent lens array 517. It also connects collet 765 to negative axicon 713 via a fiber optic lead internal to a central lumen in the lead. Negative axicon 713 is of similar structure to negative axicon 704. Flexible lead 506 is held in place by set screw 513. Flexible lead 504 is held in place by set screw 515.

Figure 8:
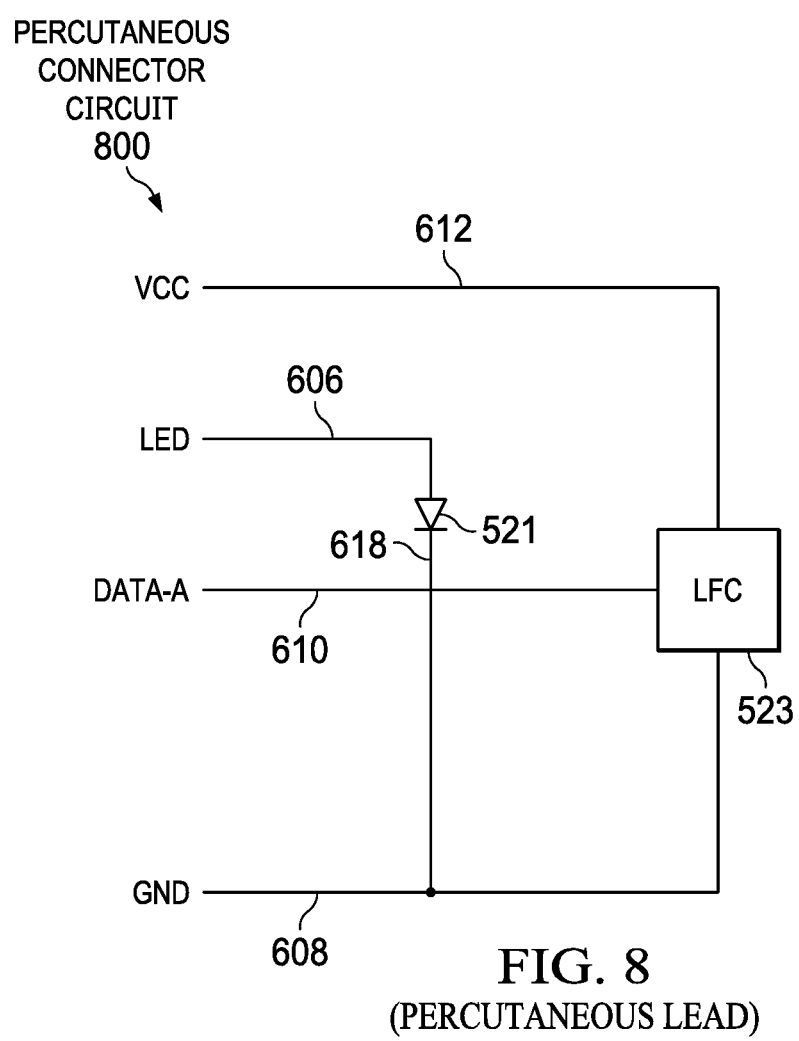
FIG. 8 is schematic of a preferred embodiment of a circuit of the percutaneous lead connector.

Referring to FIG. 8, percutaneous connector circuit 800 will be described. Percutaneous connector circuit 800 shows VCC line 612 connected to LFC 523. LFC 523 is also shown connected to data line 610 and ground line 608. LED 521 is shown connected to LED line 606 and bridge connection 618, which is also connected to ground line 608 and LFC 523.

Figure 9:
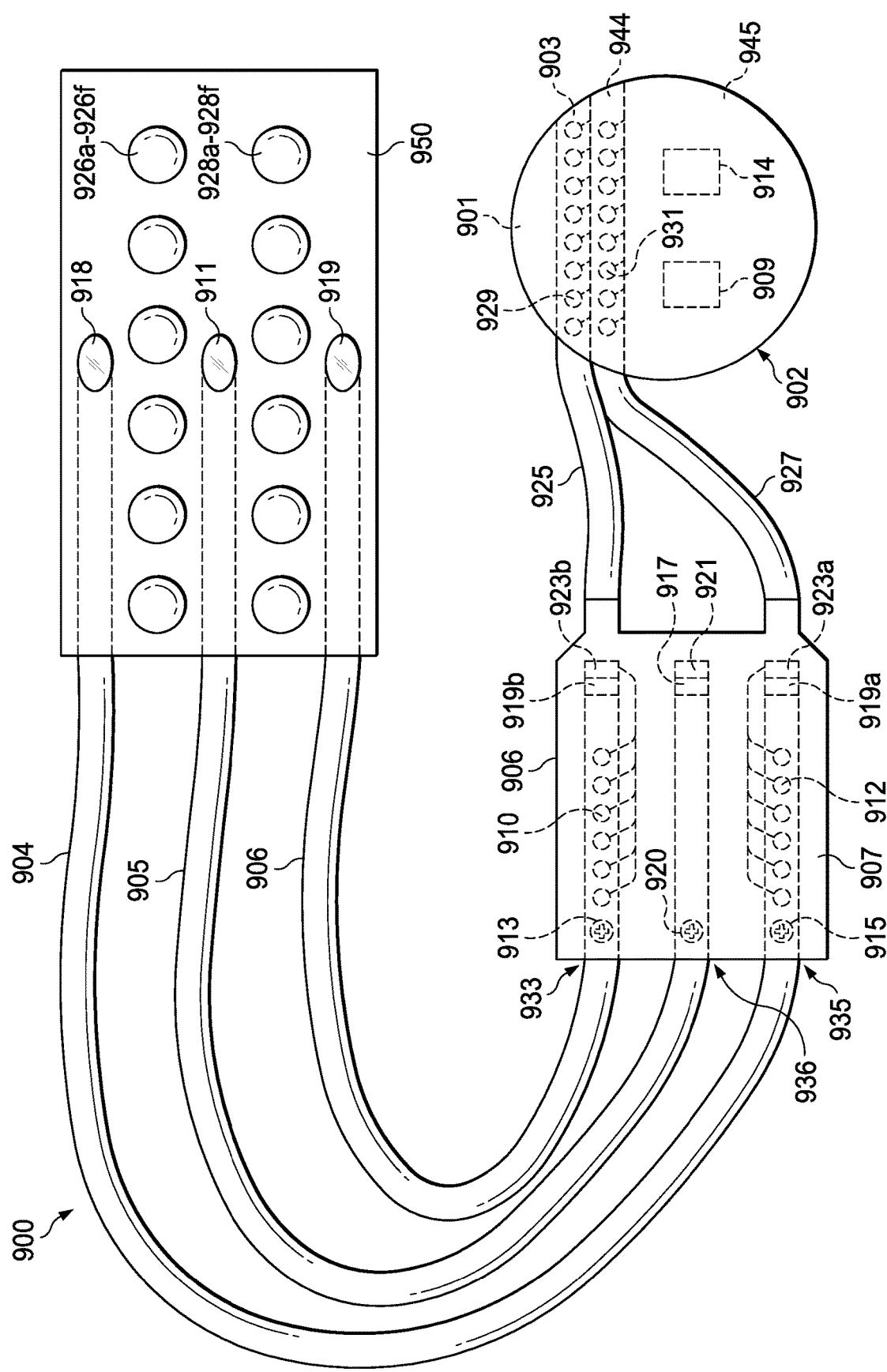
FIG. 9 is a system drawing of a preferred embodiment of a laminectomy lead connector system.

Turning then to FIG. 9, laminectomy lead connector system 900 will be described. Laminectomy lead connector system 900 is comprised of IPG 902 connected to laminectomy lead connector 916 which is in turn connected to paddle shaped laminectomy lead 950. IPG 902 is connected to laminectomy lead connector 916 by flexible lead 925 and flexible lead 927. Laminectomy lead connector 916 is connected to paddle shaped laminectomy lead 950 by flexible lead 904, flexible lead 905 and flexible lead 906.

IPG 902 comprises IPG body 945. IPG body 945 is hermetically sealed and includes battery 909 operatively connected to processor 914. In a preferred embodiment, processor 914 includes a MSP430 microprocessor core available from Texas Instruments of Dallas, Tex.

IPG 902 is connected to header 901. In a preferred embodiment, header 901 is hermetically sealed to IPG 902. Header 901 includes connector array 903 and connector array 944. In a preferred embodiment, each connector array includes eight contacts. Connector array 903 includes contacts 929. Connector array 944 includes contacts 931.

Laminectomy lead connector 916 includes connector body 907. In a preferred embodiment, connector body 907 is comprised of a flexible Silastic elastomer, polyvinyl chloride, poly (methyl methacrylate) or a suitable, biologically compatible epoxy. Connector body 907 is connected to IPG 902 through flexible lead 925 and flexible lead 927. Flexible lead 925 is connected to connector array 903. Flexible lead 927 is connected to connector array 944. Connector body 907 further comprises cylindrical port 933, cylindrical port 936 and cylindrical port 935. In a preferred embodiment, each of these cylindrical ports is approximately 1.5 millimeters in diameter (±10%).

Lens array 919a is rigidly positioned in the proximal end of cylindrical port 935, as will be further described. LFC 923a is rigidly connected to lens array 919a, as will be further described. Lens array 917 is rigidly positioned at the proximal end of cylindrical port 936. LED 921 is rigidly fixed to lens array 917, as will be further described. Lens array 919b is rigidly fixed at the proximal end of cylindrical port 933, as will be further described. LFC 923b is rigidly fixed to lens array 919b, as will be further described.

Connector body 907 supports six contacts 910 adjacent cylindrical port 933. Connector body 907 also supports six contacts 912 adjacent cylindrical port 935. Set screw 913 extends into cylindrical port 933 through a threaded hole (not shown). Set screw 920 extends into cylindrical port 936 through a threaded hole (not shown). Set screw 915 extends into cylindrical port 935 through a threaded hole (not shown). The number of contacts can vary depending on the number of electrodes.

Flexible lead 904 is integrally formed with paddle shaped laminectomy lead 950 and terminates in transparent window 918. Flexible lead 905 is integrally formed with paddle shaped laminectomy lead 950 and terminates in transparent window 911. Flexible lead 906 is integrally formed with paddle shaped laminectomy lead 950 and terminates in transparent window 919. Flexible lead 904 is connected to connector body 907 at cylindrical port 935 and held in place by set screw 915. Flexible lead 905 is connected to connector body 907 at cylindrical port 936 and is held in place by set screw 920. Flexible lead 906 is connected to connector body 907 at cylindrical port 933 and held in place by set screw 913. The number of flexible leads may vary. However, preferably there are three to provide for stereoscopic detection of the spinal cord position using near-infrared reflectometry.

Figure 10A:
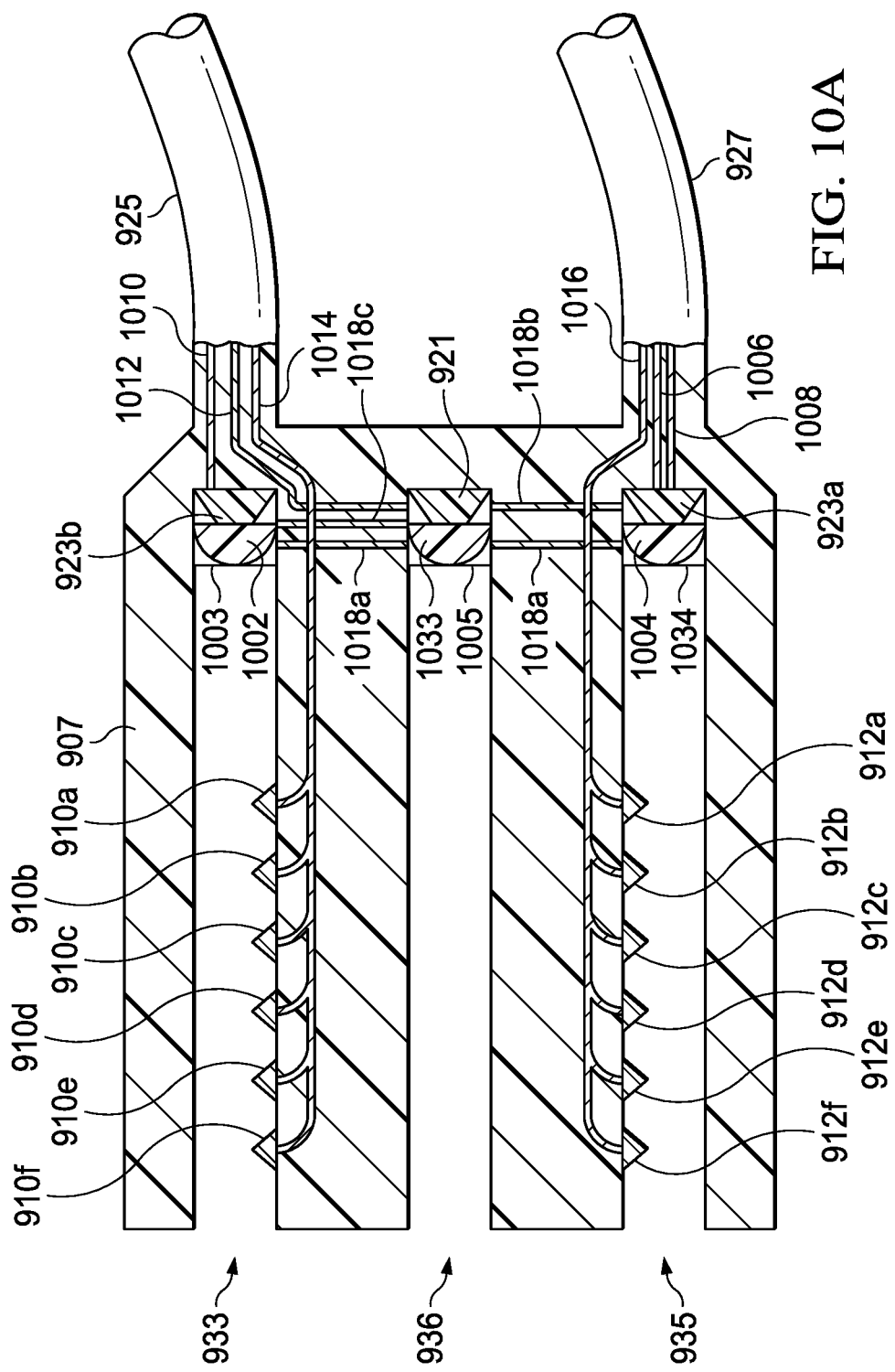
FIG. 10A is cross sectional drawing of a preferred embodiment of the laminectomy lead connector.
Figure 10B:
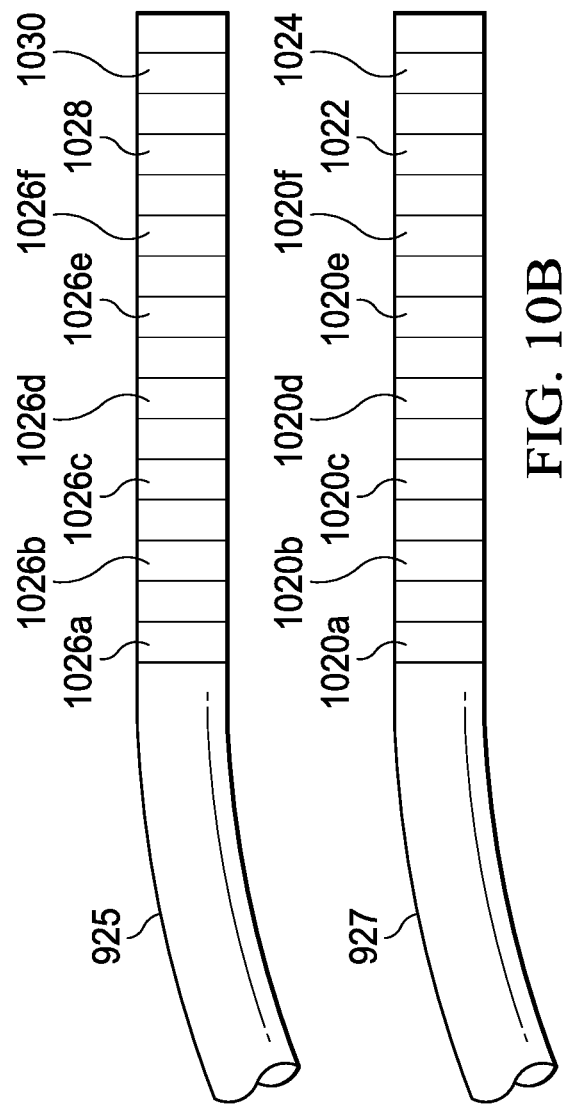
FIG. 10B is a drawing of the flexible leads of a preferred embodiment of a laminectomy lead contact.

Turning then to FIGS. 10A and 10B, connector body 907 includes integrally formed flexible lead 927 and integrally formed flexible lead 925. Integrally formed flexible lead 925 includes internal wire Data A line 1010, VCC line 1012 and electrode line bundle 1014. Electrode line bundle 1014 includes six separate wires. Data A line 1010 is connected to LFC 923b. VCC line 1012 is connected to LED 921. One wire each of electrode line bundle 1014 is connected to integrally formed contacts 910a, 910b, 910c, 910d, 910e and 910f. Integrally formed flexible lead 927 includes Data B line 1006, ground line 1008, and electrode line bundle 1016. Electrode line bundle 1016 includes six separate wires. One wire each of electrode line bundle 1016 is connected to integrally formed contact 912a, 912b, 912c, 912d, 912e and 912f. Data B line 1006 is connected to LFC 923a. Ground line 1008 is connected to LFC 923a. LFC 923a and LFC 923b are connected to LED 921 and VCC by bridge connection 1018b and bridge connection 1018c as will be further described. LFC 923a, LED 921 and LFC 923b are both connected to ground by virtue of bridge connection 1018a, as will be further described.

Connector body 907 further comprises cylindrical port 933, cylindrical port 936 and cylindrical port 935. Each of integrally formed contacts 910a-910f is positioned adjacent cylindrical port 933 and comprises a conical metallic contact formed into the connector body. Each of integrally formed contacts 910a-910f is held in a fixed positioned by connector body 907. Integrally formed contacts 912a-912f are positioned adjacent cylindrical port 935. Each of integrally formed contacts 912a-912f is held in a fixed position by connector body 907. All of the integrally formed contacts, in a preferred embodiment, are shaped as conical metallic nodes made of a platinum or platinum alloy.

Lens array 919b includes lens 1002 adjacent coupling surface 1003. In a preferred embodiment lens 1002 is arranged to collimate light from collet 1112c. In a preferred embodiment lens 1002 is formed of an optical glass encased in poly (meth methacrylate) which forms coupling surface 1003 after polishing. Lens 1002 is held adjacent LFC 923b by a suitable epoxy. Similarly, lens array 917 further comprises lens 1033 and coupling surface 1005. In a preferred embodiment, lens 1033 is an optical glass and designed to collimate light from collet 1112b. Lens 1033, in a preferred embodiment, is encased in a poly (meth methacrylate) on which forms coupling surface 1005 after polishing. In a preferred embodiment, lens 1033 is held adjacent LED 921 by a suitable epoxy. Similarly, lens array 919a is comprised of lens 1004 and coupling surface 1034. In a preferred embodiment, lens 1004 is an optical glass designed to collimate light from collet 1112a. Lens 1004 is encased in a poly (meth methacrylate) which forms a polished coupling surface 1034. In a preferred embodiment, lens 1004 is held adjacent LFC 923a by a suitable epoxy.

The proximal end of integrally formed flexible lead 925 includes cylindrical electrodes 1026a-1026f, 1028 and 1030. One wire each of electrode line bundle 1014 is connected to one of cylindrical electrodes 1026a-1026f. In a preferred embodiment, cylindrical electrode 1028 is connected to Data A line 1010. In a preferred embodiment, cylindrical electrode 1030 is connected to VCC line 1012. Likewise, flexible lead 927 includes six cylindrical electrodes 1020a-1020f, cylindrical electrode 1022 and cylindrical electrode 1024. One each of cylindrical electrodes 1020a-1020f is connected to one wire of electrode line bundle 1016. In a preferred embodiment, Data B line 1006 is connected cylindrical electrode 1022. In a preferred embodiment, ground line 1008 is connected to cylindrical electrode 1024. In this way, processor 914 can be programmed to access the VCC, data and ground lines by repurposing two each of contacts 931 and 929, which are typically used to transmit a stimulation voltage.

Figure 11A:
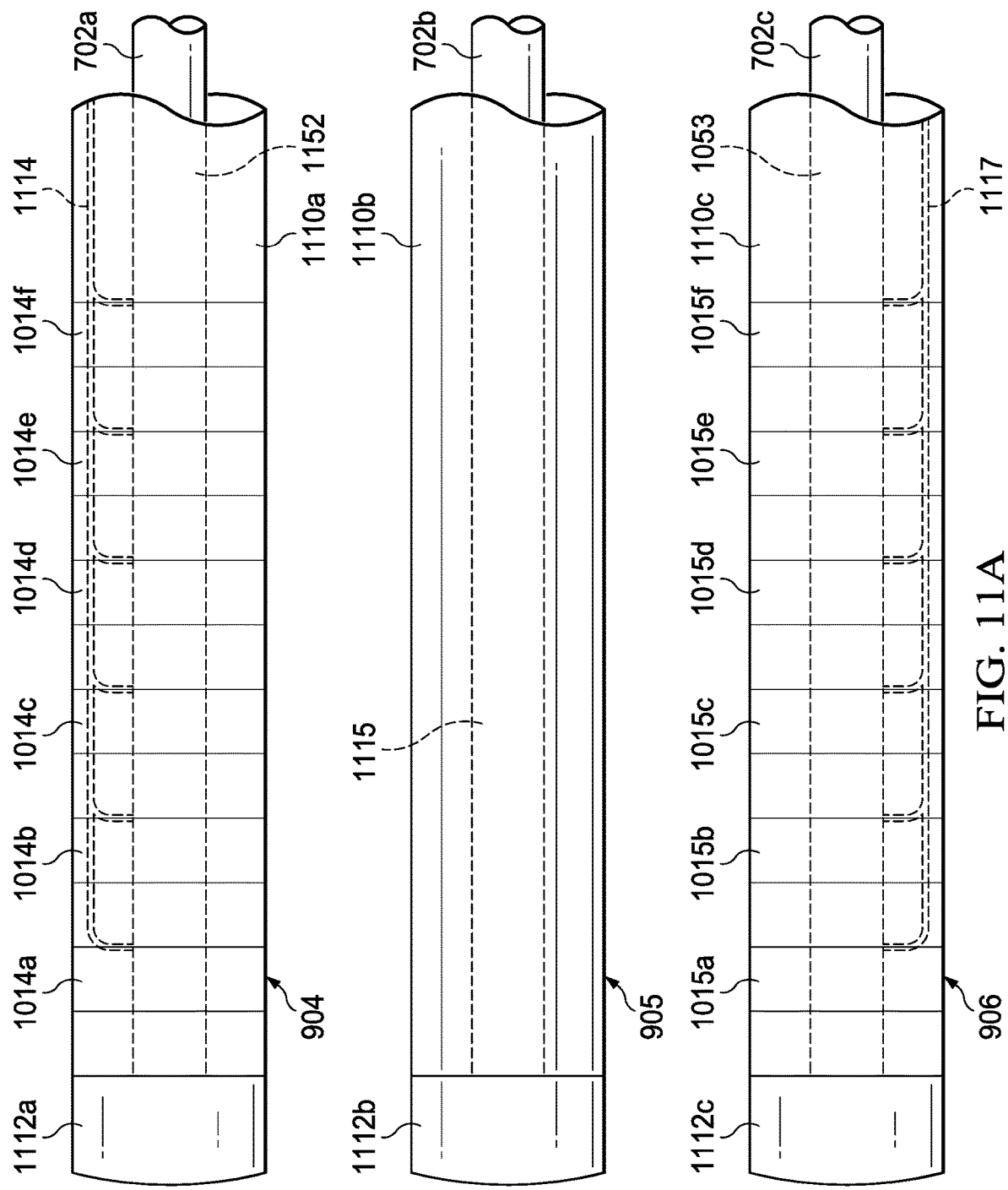
FIG. 11A is a cutaway drawing of a preferred embodiment of the flexible leads of a laminectomy lead contact.

Referring then to FIG. 11A, the proximal ends of flexible leads 904, 905 and 906 will be described. Flexible lead 904 comprises lead body 1110a. Lead body 1110a includes integrally formed electrode line bundle 1114 and optical fiber assembly 702a. Integrally formed electrode line bundle 1114 comprises six wires connected one wire each to cylindrical electrodes 1014a, 1014b, 1014c, 1014d, 1014e and 1014f. The number and positions of the wires is not critical and may vary depending on the number of electrodes required. The cylindrical electrodes are of similar composition and structure to those previously described.

Optical fiber assembly 702a comprises optical fiber 1152 integrally formed with collet 1112a. The structure of the fiber and the collet are similar to those previously described.

Flexible lead 905 further comprises lead body 1110b and integrally formed optical fiber assembly 702b. Optical fiber assembly 702b includes optical fiber 1115 integrally formed with collet 1112b. The structure and composition of the collet and the optical fiber are similar to those previously described.

Flexible lead 906 further comprises lead body 1110c and integrally formed optical fiber assembly 702c. Lead body 1110c further comprises cylindrical electrodes 1015a, 1015b, 1015c, 1015d, 1015e and 1015f. Lead body 1110c further comprises electrode line bundle 1117. In a preferred embodiment, electrode line bundle 1117 includes six individual wires, one each connected to cylindrical electrodes 1015a, 1015b, 1015c, 1015d, 1015e and 1015f. Optical fiber assembly 702c further comprises optical fiber 1053 and collet 1112c. The structure and composition of the collet, the electrodes and the optical fiber are similar to those previously described.

When assembled, collet 1112a of flexible lead 904 is nested within cylindrical port 935 adjacent coupling surface 1034 and maintained there by set screw 915. Integrally formed contact 912a is held in contact with cylindrical electrode 1014a. Similarly, integrally formed contact 912b is held in contact with cylindrical electrode 1014b, integrally formed contact 912c is held in contact with cylindrical electrode 1014c, integrally formed contact 912d is held in contact with cylindrical electrode 1014d, integrally formed contact 912e is held in contact with cylindrical electrode 1014e and integrally formed contact 912f is held in contact with cylindrical electrode 1014f.

When assembled, flexible lead 905 is held within cylindrical port 936 with collet 1112b adjacent coupling surface 1005. Flexible lead 905 is held within cylindrical port 936 by set screw 920.

When assembled, flexible lead 906 is held within cylindrical port 933 with collet 1112c held adjacent coupling surface 1003 by set screw 913. Cylindrical electrode 1015a is held in contact with integrally formed contact 910a. Similarly, cylindrical electrode 1015b is held in contact with integrally formed contact 910b, cylindrical electrode 1015c is held in contact with integrally formed contact 910c, cylindrical electrode 1015d is held in contact with integrally formed contact 910d, cylindrical electrode 1015e is held in contact with integrally formed contact 910e and cylindrical electrode 1015f is held in contact with integrally formed contact 910f.

Referring then to FIGS. 11B and 11C, paddle shaped laminectomy lead 950 will be further described. Paddle shaped laminectomy lead 950 is comprised of a flexible biocompatible sheet having components molded within it. Preferably the sheet is comprised of an inert silicon elastomer such as Silastic available from Dow Corning. In a preferred embodiment, paddle shaped laminectomy lead 950 further comprises transparent window 918, transparent window 911 and transparent window 919, attached to optical fiber assemblies 702a, 702b, and 702c, respectively. In each case, the transparent window comprises a generally cylindrical multi surface block of poly (methyl methacrylate) which is designed to fix the position the light collimator in the sheet and direct light toward the surface of the sheet. The surface of the window may be polished to retard biological fouling. In other embodiments, the light collimator may be so positioned in the sheet during manufacture that the transparent window is not used. Each of light collimators 1101, 1102, and 1103 in a preferred embodiment, is a cleaved optical fiber at 45° to the longitude and axis of the fiber. In a preferred embodiment, the beveled edge of each fiber includes a $TiO_2$ surface cladding which is comprised of nanoparticles embedded in a suitable biologically compatible epoxy. An example is shown at cleaved optical fiber 1150 on optical fiber 702c in FIG. 11C. During manufacture, the beveled edge of each fiber is positioned opposite of the electrode array plane an example of which is shown in FIG. 11C, at 1175.

Paddle shaped laminectomy lead 950 further comprises electrodes 926a-926f and 928a-928f. Each of electrodes 926a-926f and 928a-928f are exposed cylindrical metallic insets integrally molded into paddle shaped laminectomy lead 950. In a preferred embodiment, the exposed insets are convex to focus the electric field produced. In a preferred embodiment, electrodes are platinum or platinum alloy. One each of electrodes 926a-926f are connected to a single wire in electrode line bundle 1114. One each of electrodes 928a-928f is connected to a single wire in electrode line bundle 1117. The optical fibers are incorporated into the lead at the time of manufacture. The $TiO_2$ nanoparticle surface cladding is important in conversation of light intensity. Beveled edge 1175 projects the light path from the optical fiber perpendicularly in a single direction toward the surface of the electrode array.

Figure 12:
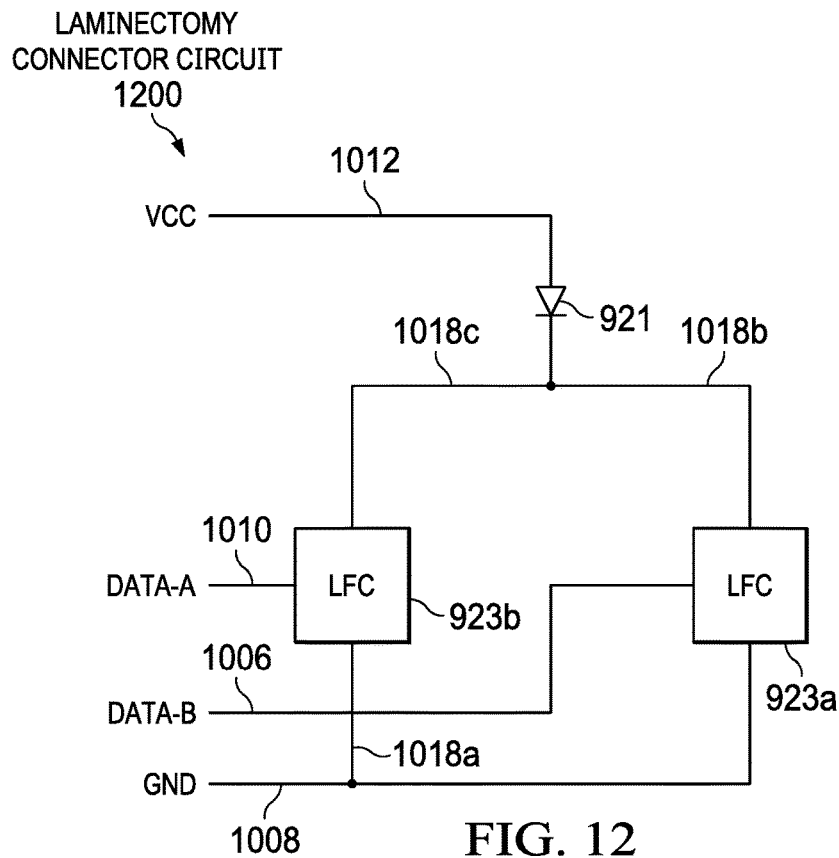
FIG. 12 is a schematic of a preferred embodiment of the laminectomy lead connector optoelectronics.

Moving on to FIG. 12, laminectomy lead connector circuit 1200 will be described. VCC line 1012 is connected to LED 921. LED 921 is also connected to LFC 923a through bridge connection 1018b. LED 921 is connected to LFC 923b through bridge connection 1018c. LFC 923a is connected to Data B line 1006. LFC 923a is also connected to ground line 1008. LFC 923b is connected to Data A line 1010. LFC 923b is also connected to ground line 1008 through bridge connection 1018a. This configuration requires a nominal 6 milliamps forward current which is efficient to drive the LED. This configuration also requires a power overhead of approximately 6.7 microwatts assuming that a 30 Hz sampling frequency, 10 microsecond duty cycle and 3.7 volts supplied.

Referring again to FIG. 5, the general operation of percutaneous connector system 500 will be described.

In use, battery 509 supplies power to processor 514, LED 521 and LFC 523. The processor in a run state generates an LED signal which is translated by the LED into infrared light energy. The light travels through flexible lead 506 where it is radiated through transparent tip 562 to impinge upon the spinal cord. Reflected light from the spinal cord enters transparent tip 520 where it is transmitted through flexible lead 504 and back to LFC 523. LFC 523 converts the reflected signal into a string of pulses of a frequency dependent upon light intensity. The frequency of these pulses is compared by the processor to a predetermined table in order to arrive at a voltage intensity and wave form for stimulation. The voltage intensity and wave form is transmitted through each of the six contacts on connector array 503 and six contacts on connector array 544, to contacts 510 and 512, respectively. The stimulation voltage and wave form reaches electrodes 504a-504f and 506a-506f, respectively, where it is delivered to the spinal cord to produce stimulation. Each of the contacts may be individually addressed for different a stimulation intensity and wave form.

Referring again to FIG. 9, the general operation of laminectomy lead connector system 900 will be described. Battery 909 provides power to processor 914, LED 921, and LFC 923b and 923a. In operation, the processor enters a run state where it sends power to LED 921. LED 921 converts the voltage to an infrared light signal which travels through flexible lead 905 and is redirected by a light collimator through transparent window 911. Once transmitted the light is reflected from the spinal cord into each of transparent windows 918 and 919. The reflected light travels down each of flexible leads 904 and 906 to LFC's 923b and 923a, respectively. Each LFC translates the light intensity into a string of pulses with a specific frequency. These pulses are transmitted through flexible leads 925 and 927, respectively to processor 914. Processor 914 reads the pulses and compares them to a table to arrive at a stimulation intensity and wave form for each electrode. A voltage corresponding to this stimulation intensity and wave form is transmitted through connector arrays 903 and 944, respectively to contacts 910 and 912 where they are sent through the flexible leads to electrodes 926 and 928, respectively, to produce stimulation. In a preferred embodiment, each of the electrodes is individually addressable and can receive a different stimulation voltage and wave form.

The relationship between incident light and reflected light and the spinal cord in each case, is described in U.S. Publication No. 2017/0252564 to Wolf the complete disclosure of which is incorporated herein by reference.

Figure 13A:
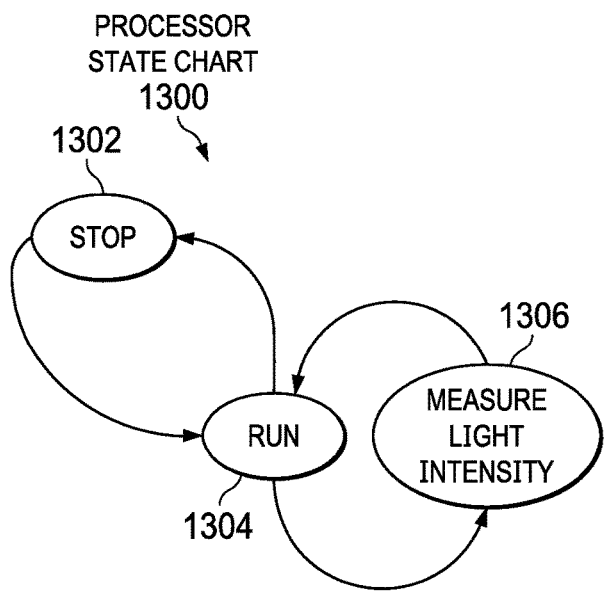
FIG. 13A is state chart of a preferred embodiment of a firmware program the processor.

Referring then to FIG. 13A a processor state chart 1300 will be described. While each of the connectors eliminates the requirement for hardware changes to the IPG, it is necessary to change existing IPG firmware to repurpose up to four channels for use by the optoelectronics in the connectors. For example, one channel must be assigned as an electrical ground or current. As another example, one or two channels must be reassigned as digital input to accept data from the LFC devices. Also, one or two channels must act as current sources to drive the optical emitter and/or detectors. The process begins at stop state 1302. The processor is powered up at stop state 1302 and then is moved to run state 1304 by a control signal. Once in run state 1304 the processor periodically moves to measure light intensity state 1306 and then returns to run state 1304. In a preferred embodiment the processor changes between run state 1304 and measure light intensity state 1306 at a rate of approximately 10 Hz.

Figure 13B:
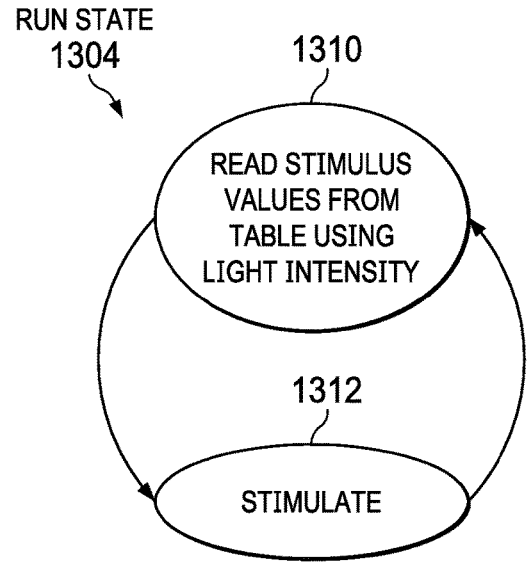
FIG. 13B is a state chart of a preferred embodiment of a firmware program of the processor.

Moving to FIG. 13B, run state 1304 will be further described. At step 1310 the processor reads a stimulus value from a table using light intensity, will be further described. At step 1312, the processor translates the stimulus value into a signal as set out in the table. A stimulation voltage and waveform is then sent to each of the electrodes as previously described. Once the stimulation is sent, the processor returns to state 1310.

Figure 14:
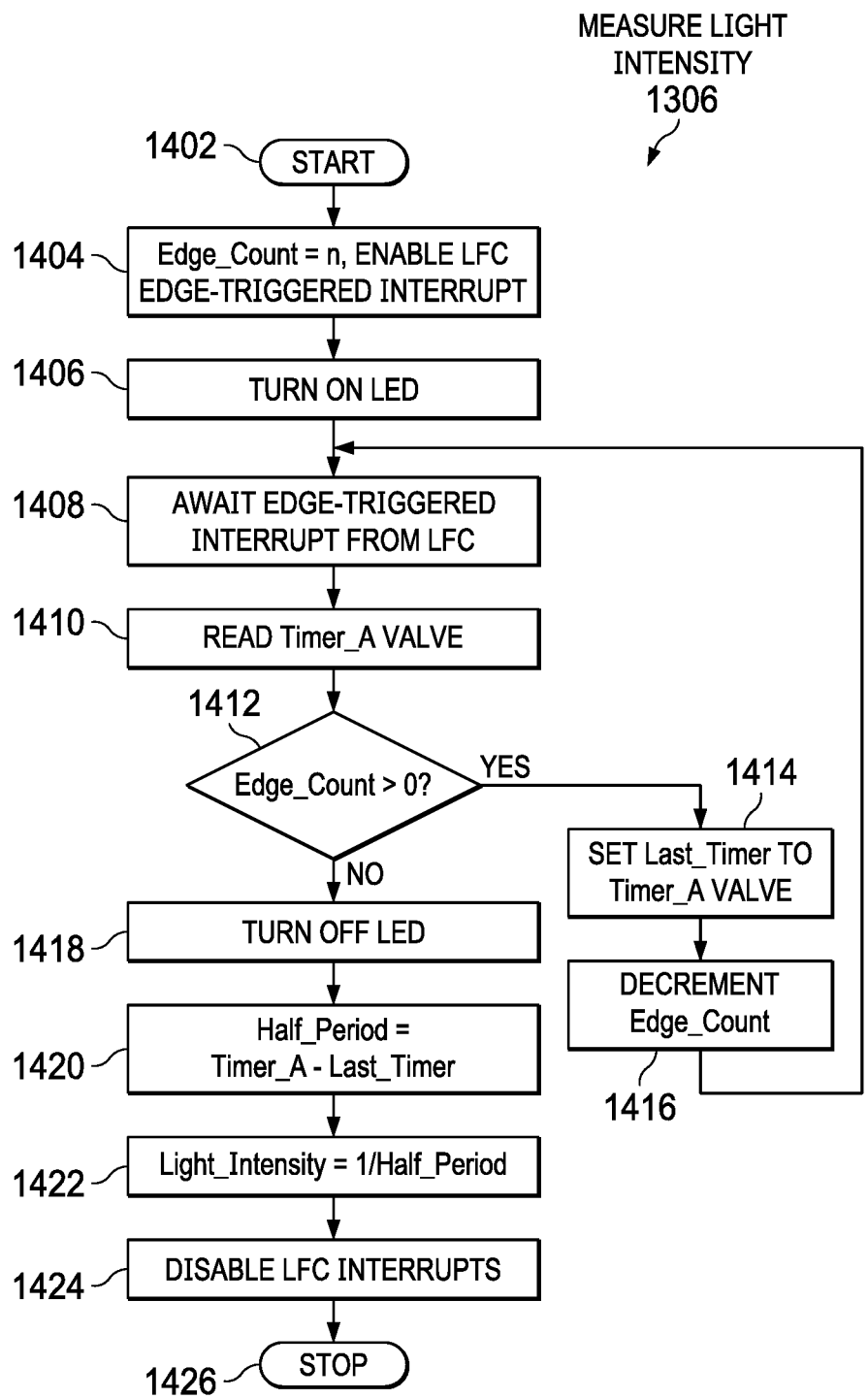
FIG. 14 is a flowchart of the "reach stimulus value" state of a preferred embodiment.

Referring then to FIG. 14, measure light intensity state 1306 will be further described. Assuming an industry standard Texas Instruments MSP430 microprocessor, the multiplexor of the processor is connected to the Data A and Data B contacts which are reconfigured to act as a set of digital inputs. The MSP430 timers A and B may be set to generate edge triggered interrupt requests in response to digital transitions on these inputs, thus providing a computationally efficient method of measuring frequency of the LFC's and thus reflected light intensity. The state is started at step 1402. At step 1404, an edge count value is set to an integer number. In a preferred embodiment N≥3 to allow for settling of the LFC. Timer A is started at zero to count forward. Timer A is a variable that represents 0 to FFFF hex and is the number of processor clock cycles between edge interrupts. At step 1404, the LFC edge triggered interrupt is also enabled.

At step 1406, the processor turns on the LED. At step 1408 the processor enters a wait state, while the timer runs waiting for an edge triggered interrupt from the LFC. When an edge triggered interrupt is received, at step 1410 the processor reads the value of timer A. At step 1412, the processor compares the value of the edge_count variable to zero. If the value is greater than zero, then the processor moves to step 1414. If the value is equal to zero, then the processor moves to step 1418. At step 1414, the timer A value is stored in the variable last timer. At step 1416, the processor then decrements the integer value of edge_count, and returns to step 1408.

At step 1418, the processor turns off the LED. At step 1420, the processor executes a binary subtraction the value of timer A from the value of last timer to arrive at a value for half period. At step 1422, a value of light intensity is set to the reciprocal of half period. At step 1424, the processor disables the edge triggered interrupt. At step 1426, the processor returns a value of light intensity and stops.

Moving to FIG. 15, an example of a light intensity table 1500 will be described. At column 1502, a light intensity for a first LFC is shown by representative values of 1 10. These values may be different. At column 1506, an electrode voltage/waveform set of values is shown for electrode 1. Likewise in column 1508 1510, 1512, 1514 and 1516 voltage waveform combinations are shown for electrode 2 through electrode 6. For embodiments with a greater or fewer number of electrodes, a greater or fewer number of columns will be provided.

At row 1518 the values for each electrode voltage and waveform are provided for a light intensity of 1. Similarly, for rows 1519-1527, values for voltage and wave form for light intensities 2-10 are shown. The voltage and wave form values are fed back to the processor at state 1310 to be used to generate a stimulation voltage and wave form at state 1312.

Figures 16, 17:
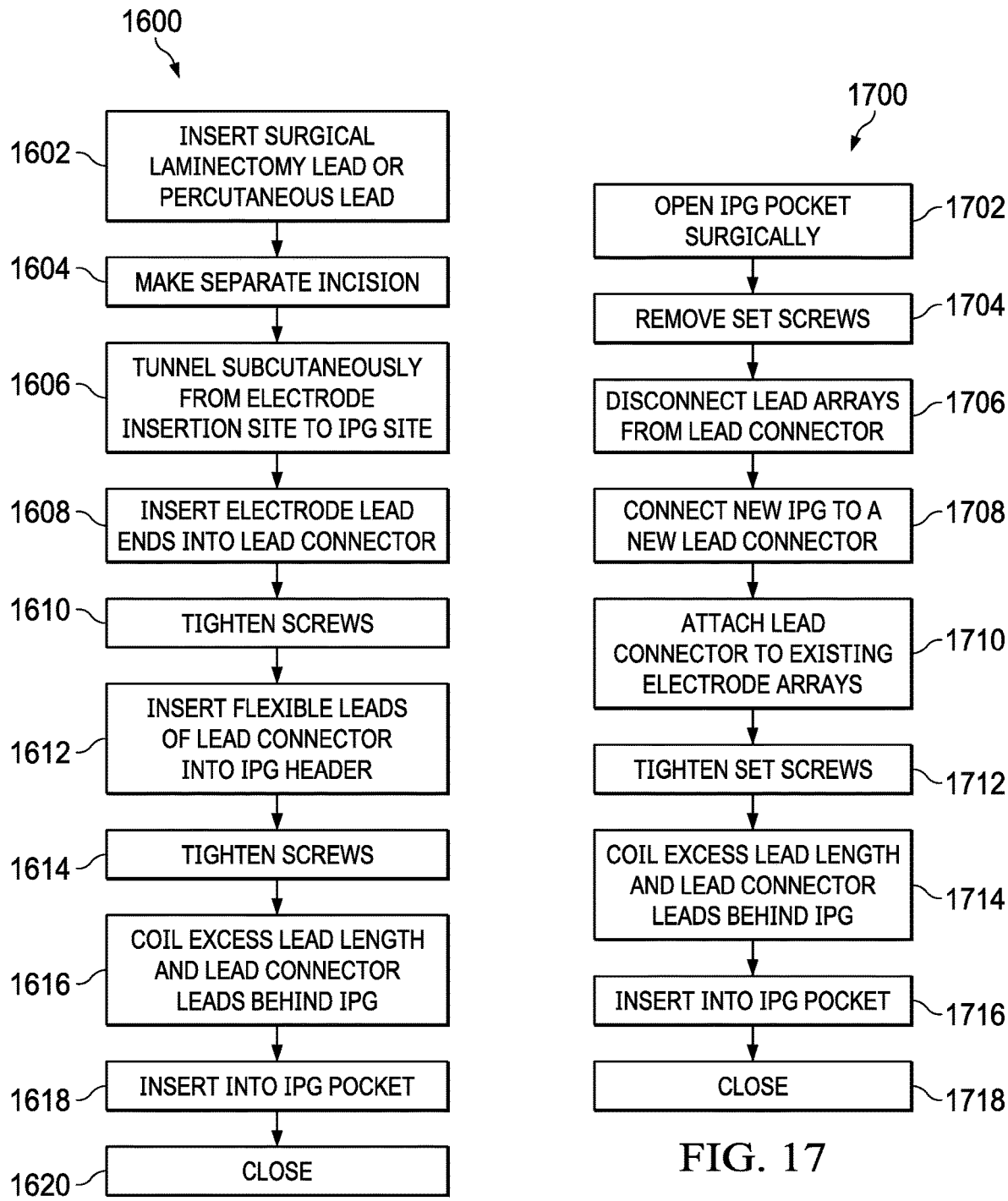
FIG. 16 is a flowchart of a preferred method of installing a lead connector of a preferred embodiment.
FIG. 17 is a flowchart of a preferred method of securing an IPG.

Referring to FIG. 16, the process 1600 for surgically inserting the IPG and laminectomy or percutaneous lead connector is described. At step 1602, the surgical laminectomy lead or percutaneous lead(s) are inserted in standard fashion and the exact procedural description is outside the scope of this document. At step 1604, a separate surgical incision is typically made in the skin of the buttock or flank to accept the IPG. At step 1606, a tunneling tool is passed subcutaneously from the electrode insertion site to the IPG site. At steps 1608 and 1610, the electrode lead ends are inserted into the lead connector and set screws are tightened. At steps 1612 and 1614, the flexible leads of the lead connector are then inserted into the IPG and the connections cinched using the IPG's integrated set screws. At steps 1616 and 1618, the excess lead length and lead connector are coiled behind the IPG and subsequently inserted into the IPG pocket. At step 1620, the incisions are then closed.

Turning to FIG. 17, method 1700 will be described. In the event that an existing SCS system needs servicing for battery replacement, at step 1702, the IPG pocket is surgically opened. At step 1704, the set screws are removed. At step 1706, the lead arrays are disconnected from the lead connector. At steps 1708, 1710 and 1712, a new IPG connected to a new lead connector assembly are then attached to the existing electrode lead arrays and the connection cinched with the lead connector set screws. At steps 1714 and 1716, the excess lead length and connector leads are coiled behind the IPG and these are reinserted into the IPG pocket. At step 1718, the incisions are closed. Thus the optoelectronics are changed out at the same time as the IPG battery replacement.

The invention claimed is:

1. A lead connector for connecting an IPG to a set of electrodes fixed on a first set of flexible leads comprising:
   a connector body;
   a set of connector ports within the connector body;
   a set of internal contacts fixed to the connector body and operationally disposed within the set of connector ports;
   a set of optoelectronics, supported by the connector body and operationally positioned in the set of connector ports;
   a second set of flexible leads, connected to the connector body;
   a first set of external contacts fixed on the second set of flexible leads;
   a second set of external contacts fixed on the second set of flexible leads;
   the second set of flexible leads further comprising a first set of wires and a second set of wires;
   wherein the first set of wires connects the set of optoelectronics to the first set of external contacts; and,
   wherein the second set of wires connects the set of internal contacts to the second set of external contacts.

2. The lead connector of claim 1, wherein:
   the set of optoelectronics further comprises at least one photo emitter and at least one photo detector.

3. The lead connector of claim 2 wherein the at least one photo emitter is a near infrared LED.

4. The lead connector of claim 3 wherein the at least one photo detector is a light to frequency converter.

5. The lead connector of claim 3 wherein the set of optoelectronics further comprises at least one lens adjacent one of the group of the at least one photo emitter and the at least one photo detector.

6. A percutaneous lead connector system for connection to an IPG, comprising:
   a connector body;
   a first connection port in the connector body;
   a second connection port in the connector body;
   a first set of internal contacts in the first connection port;
   a second set of internal contacts in the second connection port;
   an optical emitter operationally positioned in the first connection port;
   an optical detector operationally positioned in the second connection port;
   a first flexible lead, having a first set of external contacts and a second set of external contacts, attached to the connector body adjacent the first connection port;
   a second flexible lead, having a third set of external contacts and a fourth set of external contacts, attached to the connector body adjacent the second connection port;
   a first set of wires, inside the first flexible lead, connecting the optical emitter to the first set of external contacts;
   a second set of wires, inside the first flexible lead, connecting the first set of internal contacts to the second set of external contacts;
   a third set of wires, inside the second flexible lead, connecting the optical detector to the third set of external contacts; and,
   a fourth set of wires, inside the second flexible lead, connecting the second set of internal contacts to the fourth set of external contacts.

7. The percutaneous lead connector system of claim 6 further comprising a third flexible lead and a fourth flexible lead;
   the third flexible lead further comprising a first lead body with a first internal lumen;
   the fourth flexible lead further comprising a second lead body with a second internal lumen;
   a first optical fiber assembly, operationally disposed in the first internal lumen;
   a second optical fiber assembly, operationally disposed in the second internal lumen;
   a first set of lead contacts and a first set of electrodes attached to an external surface of the third flexible lead and connected together by a first set of wires within the first lead body;
   a second set of lead contacts and a second set of electrodes attached to an external surface of the fourth flexible lead and connected together by a second set of wires within the second lead body;
   wherein the first optical fiber assembly is held adjacent the optical emitter by the connector body;
   wherein the second optical fiber assembly is held adjacent the optical detector by the connector body;
   wherein the first set of lead contacts is held in contact with the first set of internal contacts by the connector body; and,
   wherein the second set of lead contacts is held in contact with the second set of internal contacts by the connector body.

8. The percutaneous lead connector system of claim 7:
   wherein the first optical fiber assembly further comprises a TiO$_2$ surfaced negative axicon.

9. The percutaneous lead connector system of claim 7:
   wherein the first optical fiber assembly further comprises a collet adjacent the optical emitter.

10. The percutaneous lead connector system of claim 7:
    wherein the first optical fiber assembly further comprises a collet adjacent the optical detector.

11. The percutaneous lead connector system of claim 6 further comprising:
    an IPG;

the IPG having a first set of IPG contacts and a second set of IPG contacts;
wherein the first set of IPG contacts is in contact with the first set of external contacts and the second set of external contacts; and,
wherein the second set of IPG contacts is in contact with the third set of external contacts and the fourth set of external contacts.

12. The percutaneous lead connector system of claim 6 wherein the optical emitter is an LED.

13. The percutaneous lead connector system of claim 6 wherein the optical detector is an LFC.

14. A laminectomy lead connection for connecting an IPG comprising:
a connector body;
a first connection port in the connector body;
a second connection port in the connector body;
a third connection port in the connector body;
a first photo detector operationally positioned in the first connection port;
a photo emitter operationally positioned in the second connection port;
a second photo detector operationally positioned in the third connection port;
a first set of internal contacts in the first connection port;
a second set of internal contacts in the third connection port;
a first flexible lead, having a first set of external contacts and a second set of external contacts, attached to the connector body;
a second flexible lead, having a third set of external contacts and a fourth set of external contacts, attached to the connector body;
wherein the first set of external contacts is electronically connected to the photo emitter and the first photo detector;
wherein the second set of external contacts is electronically connected to the first set of internal contacts;
wherein the third set of external contacts is electronically connected to the second photo detector and the photo emitter; and,
wherein the fourth set of external contacts is connected to the second set of internal contacts.

15. The laminectomy lead connection of claim 14 further comprising a fourth flexible lead, a fifth flexible lead and a sixth flexible lead;
the fourth flexible lead, attached to a flexible paddle body, further comprising a first optical fiber;
the fifth flexible lead, attached to the flexible paddle body, further comprising a second optical fiber;
the sixth flexible lead, attached to the flexible paddle body, further comprising a third optical fiber;
the flexible paddle body further comprising a first set of electrodes and a second set of electrodes;
the second optical fiber positioned in the flexible paddle body to project light generally perpendicular to the flexible paddle body;
the first optical fiber and the third optical fiber positioned in the flexible paddle body to receive light generally perpendicular to the flexible paddle body;
wherein the first set of electrodes is held in electrical contact with the first set of internal contacts;
wherein the second set of electrodes is held in electrical contact with the second set of internal contacts;
wherein the first optical fiber is held in optical contact with the first photo detector;
the second optical fiber is held in optical contact with the photo emitter; and,
the third optical fiber is held in optical contact with the second photo detector.

16. The laminectomy lead connection of claim 14 further comprising an IPG and wherein:
the IPG has a first set of IPG contacts and a second set of IPG contacts;
wherein the first set of IPG contacts is in contact with the first set of external contacts and the second set of external contacts; and,
wherein the second set of IPG contacts is in contact with the third set of external contacts and the fourth set of external contacts.

17. A laminectomy lead connector comprising:
a connector body;
a first receiver port in the connector body;
a first set of electrical contacts operatively disposed in the first receiver port;
a first axial lens array operatively disposed in the first receiver port;
a light source adjacent the first axial lens array;
a first flexible lead attached to the connector body adjacent the first receiver port;
a first electrode line bundle, sealed within the first flexible lead, connected to the first set of electrical contacts;
a first power line, sealed in the first flexible lead, connected to the light source;
a ground line, sealed in the first flexible lead, connected to the light source;
a second receiver port in the connector body;
a second set of electrical contacts operatively disposed in the second receiver port;
a second axial lens array operatively disposed in the second receiver port;
a light detector adjacent the second axial lens array;
a second flexible lead, attached to the connector body, adjacent the second receiver port;
a second electrode line bundle, sealed within the second flexible lead, connected to the second set of electrical contacts;
a data line, sealed in the second flexible lead, connected to the light detector;
a second power line, sealed in the second flexible lead, connected to the light detector;
a third set of electrical contacts, fixed on an exterior of the first flexible lead, connected to the first electrode line bundle, the first power supply line and the ground line; and,
a fourth set of electrical contacts, fixed on the exterior of the second flexible lead, connected to the second electrode line bundle, the second power supply line and the data line.

18. The connector of claim 17, wherein the first axial lens array further comprises a collimating lens.

19. The connector of claim 17, wherein the light source is an LED.

20. The connector of claim 17, wherein the light detector is a light to frequency converter.

21. The connector of claim 17, further comprising:
a third flexible lead, connected to the first receiver port;
a fifth set of electrical contacts, fixed on the exterior of the third flexible lead, and held in contact with the first set of electrical contacts;
a third electrode line bundle, sealed in the third flexible lead, connected to the fifth set of electrical contacts;

a first set of electrodes, fixed on an exterior surface of the third flexible lead, and connected to the third electrode line bundle;
a first optical transmission line, sealed in the third flexible lead, adjacent the first axial lens array;
a light dispersion element, fixed on the third flexible lead, operatively connected to the first optical transmission line;
a fourth flexible lead, connected to the second receiver port;
a sixth set of electrical contacts, fixed on the exterior of the fourth flexible lead, and held in contact with the second set of electrical contacts;
a fourth electrode line bundle, sealed in the fourth flexible lead, connected to the sixth set of electrical contacts;
a second set of electrodes, fixed on the exterior of the fourth flexible lead, and connected to the fourth electrode line bundle;
a second optical transmission line, sealed in the fourth flexible lead, adjacent the second axial lens array; and,
a light collection element, fixed on the fourth flexible lead, operatively connected to the second optical transmission line.

22. The connector of claim 21 wherein the light dispersion element further comprises a negative axicon.

23. The connector of claim 21 wherein the light collection element further comprises a negative axicon.

24. A laminectomy lead connector comprising:
a connector body;
a first receiver port in the connector body;
a first set of electrical contacts operatively disposed in the first receiver port;
a first axial lens array operatively disposed in the first receiver port;
a light source adjacent the first axial lens array;
a first flexible lead attached to the connector body adjacent the first receiver port;
a first electrode line bundle, sealed within the first flexible lead, connected to the first set of electrical contacts;
a first power line, sealed in the first flexible lead, connected to the light source;
a ground line, sealed in the first flexible lead, connected to the light source;
a second receiver port in the connector body;
a second set of electrical contacts operatively disposed in the second receiver port;
a second axial lens array operatively disposed in the second receiver port;
a light detector adjacent the second axial lens array;
a second flexible lead, attached to the connector body, adjacent the second receiver port;
a second electrode line bundle, sealed within the second flexible lead, connected to the second set of electrical contacts;
a data line, sealed in the second flexible lead, connected to the light detector;
a second power line, sealed in the second flexible lead, connected to the light detector;
a third set of electrical contacts, fixed on an exterior of the first flexible lead, connected to the first electrode line bundle, the first power line and the ground line;
a fourth set of electrical contacts, fixed on the exterior of the second flexible lead, connected to the second electrode line bundle, the second power line and the data line;
a third flexible lead, connected to the first receiver port;
a fifth set of electrical contacts, fixed on the exterior of the third flexible lead, and held in contact with the first set of electrical contacts;
a third electrode line bundle, sealed in the third flexible lead, connected to the fifth set of electrical contacts;
a first set of electrodes, fixed on an exterior surface of the third flexible lead, and connected to the third electrode line bundle;
a first optical transmission line, sealed in the third flexible lead, adjacent the first axial lens array;
a light dispersion element, fixed on the third flexible lead, operatively connected to the first optical transmission line;
a fourth flexible lead, connected to the second receiver port;
a sixth set of electrical contacts, fixed on the exterior of the fourth flexible lead, and held in contact with the second set of electrical contacts;
a fourth electrode line bundle, sealed in the fourth flexible lead, connected to the sixth set of electrical contacts;
a second set of electrodes, fixed on the exterior of the fourth flexible lead, and connected to the fourth electrode line bundle;
a second optical transmission line, sealed in the fourth flexible lead, adjacent the second axial lens array;
a light collection element, fixed on the fourth flexible lead, operatively connected to the second optical transmission line;
a computer processor operatively connected to the first power line, the data line, the first electrode line bundle and the second electrode line bundle;
the computer processor programmed to:
  activate the light source;
  receive a data signal from the data line;
  calculate a first stimulation signal strength based on the data signal;
  calculate a second stimulation signal strength based on the data signal;
  send the first stimulation signal to the first set of electrodes on the first electrode line bundle; and,
  send the second stimulation signal to the second set of electrodes on the second electrode line bundle.

25. A laminectomy lead connector comprising:
a connector body;
a first receiver port in the connector body;
a first set of electrical contacts operatively disposed in the first receiver port;
a first axial lens array operatively disposed in the first receiver port;
a light source adjacent the first axial lens array;
a first flexible lead attached to the connector body adjacent the first receiver port;
a first electrode line bundle, sealed within the first flexible lead, connected to the first set of electrical contacts;
a first power line, sealed in the first flexible lead, connected to the light source;
a ground line, sealed in the first flexible lead, connected to the light source;
a second receiver port in the connector body;
a second set of electrical contacts operatively disposed in the second receiver port;
a second axial lens array operatively disposed in the second receiver port;
a light detector adjacent the second axial lens array;
a second flexible lead, attached to the connector body, adjacent the second receiver port;

a second electrode line bundle, sealed within the second flexible lead, connected to the second set of electrical contacts;

a data line, sealed in the second flexible lead, connected to the light detector;

a second power line, sealed in the second flexible lead, connected to the light detector;

a third set of electrical contacts, fixed on an exterior of the first flexible lead, connected to the first electrode line bundle, the first power line and the ground line;

a fourth set of electrical contacts, fixed on the exterior of the second flexible lead, connected to the second electrode line bundle, the second power line and the data line;

a third flexible lead, connected to the first receiver port;

a fifth set of electrical contacts, fixed on the exterior of the third flexible lead, and held in contact with the first set of electrical contacts;

a third electrode line bundle, sealed in the third flexible lead, connected to the fifth set of electrical contacts;

a first set of electrodes, fixed on an exterior surface of the third flexible lead, and connected to the third electrode line bundle;

a first optical transmission line, sealed in the third flexible lead, adjacent the first axial lens array;

a light dispersion element, fixed on the third flexible lead, operatively connected to the first optical transmission line;

a fourth flexible lead, connected to the second receiver port;

a sixth set of electrical contacts, fixed on the exterior of the fourth flexible lead, and held in contact with the second set of electrical contacts;

a fourth electrode line bundle, sealed in the fourth flexible lead, connected to the sixth set of electrical contacts;

a second set of electrodes, fixed on the exterior of the fourth flexible lead, and connected to the fourth electrode line bundle;

a second optical transmission line, sealed in the fourth flexible lead, adjacent the second axial lens array;

a light collection element, fixed on the fourth flexible lead, operatively connected to the second optical transmission line;

a computer processor operatively connected to the light source and the light detector;

the computer processor programmed to:
measure a light intensity from the light source;
read a set of stimulus values from a table based on the light intensity; and,
send a set of stimulus signals to the first set of electrodes based on the set of stimulus values.

26. The connector of claim 25 wherein the computer processor is further programmed to:
send the set of stimulus signals to the second set of electrodes based on the set of stimulus values.

27. The connector of claim 25 wherein the set of stimulus values further comprises a voltage value and a waveform value.

28. A laminectomy lead connector comprising:
a connector body;
a first receiver port in the connector body;
a first set of electrical contacts operatively disposed in the first receiver port;
a first axial lens array operatively disposed in the first receiver port;
a first light detector adjacent the first axial lens array;
a first flexible lead, attached to the connector body;
a first electrode line bundle, sealed within the first flexible lead, connected to the first set of electrical contacts;
a power supply line, sealed in the first flexible lead, connected to the first light detector;
a first data line, sealed in the first flexible lead, connected to the first light detector;
a second receiver port in the connector body;
a second axial lens array operatively disposed in the second receiver body port;
a light source, adjacent the second axial lens array, connected to the power supply line;
a third receiver port in the connector body;
a second set of electrical contacts operatively disposed in the third receiver port;
a third axial lens array operatively disposed in the third receiver port;
a second light detector, adjacent the third axial lens array, connected to the power supply line;
a second flexible lead, attached to the connector body;
a second electrode line bundle, sealed within the second flexible lead, connected to the second set of electrical contacts;
a ground line, sealed within the second flexible lead, connected to the first light detector, the second light detector and the light source;
a second data line, sealed in the second flexible lead, connected to the second light detector;
a third set of electrical contacts, fixed on an exterior of the first flexible lead, connected to the first electrode line bundle, the power supply line and the first data line; and,
a fourth set of electrical contacts, fixed on the exterior of the second flexible lead, connected to the second electrode line bundle, the ground line and the second data line.

29. The connector of claim 28 wherein the first axial lens array further comprises a first collimating lens and wherein the second axial lens array comprises a second collimating lens.

30. The connector of claim 28 wherein the light source is an LED.

31. The connector of claim 28 wherein the first light detector is a first light to frequency converter and wherein the second light detector is a second light to frequency converter.

32. The connector of claim 28 further comprising:
a flexible paddle;
a first set of electrodes fixed in the flexible paddle;
a second set of electrodes fixed in the flexible paddle;
a first optical guide, fixed in the flexible paddle, adjacent the first set of electrodes;
a second optical guide, fixed in the flexible paddle, adjacent the first set of electrodes and the second set of electrodes;
a third optical guide, fixed in the flexible paddle, adjacent the second set of electrodes;
a third flexible lead, attached to the flexible paddle and to the third receiver port;
a fifth set of electrical contacts, operatively disposed on the exterior of the third flexible lead and in contact with the second set of electrical contacts;
a third electrode line bundle, sealed in the third flexible lead, connected to the first set of electrodes and the fifth set of electrical contacts;
a first collet, attached to the third flexible lead, adjacent the third axial lens array;

a first optical transmission line, sealed in the third flexible lead, attached to the first collet and the first optical guide;
a fourth flexible lead, attached to the flexible paddle and the second receiver port;
a second collet, attached to the fourth flexible lead, adjacent the second axial lens array;
a second optical transmission line, sealed in the fourth flexible lead, attached to the second collet and the second optical guide;
a fifth flexible lead, attached to the flexible paddle and to the first receiver port;
a sixth set of electrical contacts, operatively disposed on the exterior of the fifth flexible lead and in contact with the first set of electrical contacts;
a fourth electrode line bundle, sealed in the fifth flexible lead, connected to the second set of electrodes and the sixth set of electrical contacts;
a third collet, attached to the fifth flexible lead, adjacent the first axial lens array; and,
a third optical transmission line, sealed in the fifth flexible lead, attached to the third collet and the third optical guide.

33. The connector of claim 32 wherein the first optical guide further comprises a beveled edge of the first optical transmission line clad with titanium dioxide.

34. The connector of claim 32 wherein the first optical guide further comprises a light collimator.

35. The connector of claim 32 wherein the flexible paddle further comprises a silastic polymer.

36. A laminectomy lead connector comprising:
a connector body;
a first receiver port in the connector body;
a first set of electrical contacts operatively disposed in the first receiver port;
a first axial lens array operatively disposed in the first receiver port;
a first light detector adjacent the first axial lens array;
a first flexible lead, attached to the connector body;
a first electrode line bundle, sealed within the first flexible lead, connected to the first set of electrical contacts;
a power supply line, sealed in the first flexible lead, connected to the first light detector;
a first data line, sealed in the first flexible lead, connected to the first light detector;
a second receiver port in the connector body;
a second axial lens array operatively disposed in the second receiver port;
a light source, adjacent the second axial lens array, connected to the power supply line;
a third receiver port in the connector body;
a second set of electrical contacts operatively disposed in the third receiver port;
a third axial lens array operatively disposed in the third receiver port;
a second light detector, adjacent the third axial lens array, connected to the power supply line;
a second flexible lead, attached to the connector body;
a second electrode line bundle, sealed within the second flexible lead, connected to the second set of electrical contacts;
a ground line, sealed within the second flexible lead, connected to the first light detector, the second light detector and the light source;
a second data line, sealed in the second flexible lead, connected to the second light detector;
a third set of electrical contacts, fixed on an exterior of the first flexible lead, connected to the first electrode line bundle, the power supply line and the first data line;
a fourth set of electrical contacts, fixed on the exterior of the second flexible lead, connected to the second electrode line bundle, the ground line and the second data line;
a flexible paddle;
a first set of electrodes fixed in the flexible paddle;
a second set of electrodes fixed in the flexible paddle;
a first optical guide, fixed in the flexible paddle, adjacent the first set of electrodes;
a second optical guide, fixed in the flexible paddle, adjacent the first set of electrodes and the second set of electrodes;
a third optical guide, fixed in the flexible paddle, adjacent the second set of electrodes;
a third flexible lead, attached to the flexible paddle and to the third receiver port;
a fifth set of electrical contacts, operatively disposed on an exterior of the third flexible lead and in contact with the second set of electrical contacts;
a third electrode line bundle, sealed in the third flexible lead, connected to the first set of electrodes and the fifth set of electrical contacts;
a first collet, attached to the third flexible lead, adjacent the third axial lens array;
a first optical transmission line, sealed in the third flexible lead, attached to the first collet and the first optical guide;
a fourth flexible lead, attached to the flexible paddle and the second receiver port;
a second collet, attached to the fourth flexible lead, adjacent the second axial lens array;
a second optical transmission line, sealed in the fourth flexible lead, attached to the second collet and the second optical guide;
a fifth flexible lead, attached to the flexible paddle and to the first receiver port;
a sixth set of electrical contacts, operatively disposed on the exterior of the fifth flexible lead and in contact with the first set of electrical contacts;
a fourth electrode line bundle, sealed in the fifth flexible lead, connected to the second set of electrodes and the sixth set of electrical contacts;
a third collet, attached to the fifth flexible lead, adjacent the first axial lens array;
a third optical transmission line, sealed in the fifth flexible lead, attached to the third collet and the third optical guide; and,
a computer processor operatively connected to the first data line, the second data line, the first electrode line bundle and the second electrode line bundle;
the computer processor programmed to:
activate the light source;
receive a first data signal from the first data line;
receive a second data signal from the second data line;
calculate a first stimulation signal based on at least one of the group of the first data signal and the second data signal;
calculate a second stimulation signal based on at least one of the group of the first data signal and the second data signal;
send the first stimulation signal to the first electrode line bundle; and,
send the second stimulation signal to the second electrode line bundle.

37. A laminectomy lead connector comprising:
a connector body;
a first receiver port in the connector body;
a first set of electrical contacts operatively disposed in the first receiver port;
a first axial lens array operatively disposed in the first receiver port;
a first light detector adjacent the first axial lens array;
a first flexible lead, attached to the connector body;
a first electrode line bundle, sealed within the first flexible lead, connected to the first set of electrical contacts;
a power supply line, sealed in the first flexible lead, connected to the first light detector;
a first data line, sealed in the first flexible lead, connected to the first light detector;
a second receiver port in the connector body;
a second axial lens array operatively disposed in the second receiver port;
a light source, adjacent the second axial lens array, connected to the power supply line;
a third receiver port in the connector body;
a second set of electrical contacts operatively disposed in the third receiver port;
a third axial lens array operatively disposed in the third receiver port;
a second light detector, adjacent the third axial lens array, connected to the power supply line;
a second flexible lead, attached to the connector body;
a second electrode line bundle, sealed within the second flexible lead, connected to the second set of electrical contacts;
a ground line, sealed within the second flexible lead, connected to the first light detector, the second light detector and the light source;
a second data line, sealed in the second flexible lead, connected to the second light detector;
a third set of electrical contacts, fixed on an exterior of the first flexible lead, connected to the first electrode line bundle, the power supply line and the first data line;
a fourth set of electrical contacts, fixed on the exterior of the second flexible lead, connected to the second electrode line bundle, the ground line and the second data line;
a flexible paddle;
a first set of electrodes fixed in the flexible paddle;
a second set of electrodes fixed in the flexible paddle;
a first optical guide, fixed in the flexible paddle, adjacent the first set of electrodes;
a second optical guide, fixed in the flexible paddle, adjacent the first set of electrodes and the second set of electrodes;
a third optical guide, fixed in the flexible paddle, adjacent the second set of electrodes;
a third flexible lead, attached to the flexible paddle and to the third receiver port;
a fifth set of electrical contacts, operatively disposed on the exterior of the third flexible lead and in contact with the second set of electrical contacts;
a third electrode line bundle, sealed in the third flexible lead, connected to the first set of electrodes and the fifth set of electrical contacts;
a first collet, attached to the third flexible lead, adjacent the third axial lens array;
a first optical transmission line, sealed in the third flexible lead, attached to the first collet and the first optical guide;
a fourth flexible lead, attached to the flexible paddle and the second receiver port;
a second collet, attached to the fourth flexible lead, adjacent the second axial lens array;
a second optical transmission line, sealed in the fourth flexible lead, attached to the second collet and the second optical guide;
a fifth flexible lead, attached to the flexible paddle and to the first receiver port;
a sixth set of electrical contacts, operatively disposed on the exterior of the fifth flexible lead and in contact with the first set of electrical contacts;
a fourth electrode line bundle, sealed in the fifth flexible lead, connected to the second set of electrodes and the sixth set of electrical contacts;
a third collet, attached to the fifth flexible lead, adjacent the first axial lens array;
a third optical transmission line, sealed in the fifth flexible lead, attached to the third collet and the third optical guide;
a computer processor operatively connected to the light source, the first light detector and the second light detector;
the computer processor programmed to:
measure a first light intensity from the first light detector;
measure a second light intensity from the second light detector;
read a first set of stimulus values from a table based on the first light intensity;
read a second set of stimulus values from the table based on the second light intensity;
send a first set of stimulus signals to the first set of electrodes based on the first set of stimulus values; and,
send a second set of stimulus to the second set of electrodes based on the second set of stimulus values.

38. The connector of claim 37 wherein the first set of stimulus values further comprises a voltage value and a waveform value.

39. The connector of claim 37 wherein the computer processor is further programmed to measure the first light intensity by:
setting an edge count value;
activating the light source;
awaiting an edge triggered interrupt;
reading a timer value;
comparing the edge count value to zero;
if the edge count value is greater than zero then setting a last timer value to the timer value and decrementing the edge count value;
if the edge count value is not greater than zero then:
deactivating the light source;
setting a half period value according to a first equation:

half period value=timer value− last timer value setting the first light intensity according to a second equation:

first light intensity=1/half period value.

40. A laminectomy lead system comprising:
an IPG;
an IPG header fixed to the IPG, wherein the IPG header further comprises a first connector array and a second connector array;
a connector body;
a set of flexible connector leads connecting the connector body to the IPG header;

wherein the set of flexible connector leads further comprises a first flexible lead connected to the first connector array, and a second flexible lead connected to the second connector array;
wherein the first connector array further comprises a first set of stimulation signal connectors, a light signal connector and a ground connector;
wherein the second connector array further comprises a second set of stimulation signal connectors, a data signal connector and a power connector;
a light source connected to the light signal connector;
a light detector connected to the data signal connector, and,
a set of laminectomy leads connected to the connector body.

41. The laminectomy lead system of claim 40 wherein the connector body further comprises:
a first cylindrical port, adjacent the first flexible lead; and,
a second cylindrical port, adjacent the second flexible lead.

42. The laminectomy lead system of claim 41 wherein the set of laminectomy leads further comprises:
a first laminectomy lead removably connected to the first cylindrical port; and,
a second laminectomy lead removably connected to the second cylindrical port.

43. The laminectomy lead system of claim 42 where the first laminectomy lead further comprises:
a first set of individually addressable electrodes and a first optical transmission fiber terminating in a first light dispersion element; and,
the second laminectomy lead further comprises a second set of individually addressable electrodes and a second optical transmission fiber terminating in a second light dispersion element.

44. The laminectomy lead system of claim 43 wherein the connector body further comprises:
a first electrical contact means for connecting the first set of individually addressable electrodes to the first set of stimulation signal connectors;
a second electrical contact means for connecting the second set of individually addressable electrodes to the second set of stimulation signal connectors;
a first optical connection means for connecting the light source to the first optical transmission fiber; and,
a second optical connection means for connecting the light detector to the second optical transmission fiber.

45. A laminectomy lead system comprising:
an IPG;
an IPG header fixed to the IPG, wherein the IPG header further comprises a first connector array and a second connector array;
a connector body;
a set of flexible connector leads connecting the connector body to the IPG header;
wherein the set of flexible connector leads further comprises a first flexible lead connected to the first connector array, and a second flexible lead connected to the second connector array;
wherein the first connector array further comprises a first set of stimulation signal connectors, a light signal connector and a ground connector;
wherein the second connector array further comprises a second set of stimulation signal connectors, a data signal connector and a power connector;
a light source connected to the light signal connector;
a light detector connected to the data signal connector,
a set of laminectomy leads connected to the connector body;
wherein the connector body further comprises a first cylindrical port, adjacent the first flexible lead, and a second cylindrical port, adjacent the second flexible lead;
wherein the set of laminectomy leads further comprises a first laminectomy lead removably connected to the first cylindrical port, and a second laminectomy lead removably connected to the second cylindrical port;
the first laminectomy lead further comprises a first set of individually addressable electrodes and a first optical transmission fiber terminating in a first light dispersion element the second laminectomy lead further comprises a second set of individually addressable electrodes and a second optical transmission fiber terminating in a second light dispersion element;
wherein the connector body further comprises:
a first electrical contact means for connecting the first set of individually addressable electrodes to the first set of stimulation signal connectors;
a second electrical contact means for connecting the second set of individually addressable electrodes to the second set of stimulation signal connectors;
a first optical connector means for connecting the light source to the first optical transmission fiber;
a second optical connector means for connecting the light detector to the second optical transmission fiber;
wherein the IPG further comprises a computer processor programmed to:
activate the light source to emit light through the first optical connector means;
receive data related to the light from the light detector through the second optical connector means;
calculate a first set of stimulation signals based on the data;
calculate a second set of stimulation signals based on the data;
send the first set of stimulation signals to the first set of individual addressable electrodes through the first electrical contact means; and,
send the second set of stimulation signals to the second set of individually addressable electrodes through the second electrical contact means.

46. A laminectomy lead system comprising:
an IPG;
an IPG header fixed to the IPG, wherein the IPG header further comprises a first connector array and a second connector array;
a connector body;
a set of flexible connector leads connecting the connector body to the IPG header;
wherein the set of flexible connector leads further comprises a first flexible lead connected to the first connector array, and a second flexible lead connected to the second connector array;
wherein the first connector array further comprises a first set of stimulation signal connectors, a first data line connector and a power connector;
wherein the second connector array further comprises a second set of stimulation signal connectors, a second data line connector and a ground connector;
a light source connected to the power connector;
a first light detector connected to the first data line connector, a second light detector connected to the second data line connector; and,
a set of laminectomy leads connected to the connector body.

47. The laminectomy lead system of claim 46 wherein the set of laminectomy leads comprises a first laminectomy lead, a second laminectomy lead, and a third laminectomy lead and the connector body further comprises:
a first cylindrical port;
the first laminectomy lead removably connected to the first cylindrical port;
a second cylindrical port;
the second laminectomy lead removably connected to the second cylindrical port;
a third cylindrical port; and,
the third laminectomy lead removably connected to the third cylindrical port.

48. The laminectomy lead system of claim 47 further comprising:
a silastic sheet;
a first set of electrodes embedded in the silastic sheet;
a second set of electrodes embedded in the silastic sheet;
a first optical director embedded in the silastic sheet adjacent the first set of electrodes;
a second optical director embedded in the silastic sheet adjacent the first set of electrodes and the second set of electrodes; and,
a third optical director embedded in the silastic sheet adjacent the second set of electrodes.

49. The laminectomy lead system of claim 48 wherein the first laminectomy lead further comprises:
a first set of individually addressable electrode lines connected to the first set of electrodes and a first optical transmission fiber connected to the first optical director;
the second laminectomy lead further comprises a second optical transmission fiber connected to the second optical director; and,
the third laminectomy lead further comprises a second set of individually addressable electrode lines connected to the second set of electrodes and a third optical transmission fiber connected to the third optical director.

50. The laminectomy lead system of claim 49 wherein the connector body further comprises:
a first electrical contact means for connecting the first set of individually addressable electrode lines to the first set of stimulation signal connectors;
a second electrical contact means for connecting the second set of individually addressable electrode lines to the second set of stimulation signal connectors;
a first optical connection means for connecting the first light detector to the first optical transmission fiber;
a second optical connection means for connecting the light source to the second optical transmission fiber; and,
a third optical connection means for connecting the second light detector to the third optical transmission fiber.

51. A laminectomy lead system comprising:
an IPG;
an IPG header fixed to the IPG, wherein the IPG header further comprises a first connector array and a second connector array;
a connector body;
a set of flexible connector leads connecting the connector body to the IPG header;
wherein the set of flexible connector leads further comprises a first flexible lead connected to the first connector array, and a second flexible lead connected to the second connector array;
wherein the first connector array further comprises a first set of stimulation signal connectors, a first data line connector and a power connector;
wherein the second connector array further comprises a second set of stimulation signal connectors, a second data line connector and a ground connector;
a light source connected to the power connector;
a first light detector connected to the first data line connector,
a second light detector connected to the second data line connector;
a set of laminectomy leads connected to the connector body comprising a first laminectomy lead, a second laminectomy lead, and a third laminectomy lead;
wherein the connector body further comprises:
a first cylindrical port;
the first laminectomy lead removably connected to the first cylindrical port;
a second cylindrical port;
the second laminectomy lead removably connected to the second cylindrical port;
a third cylindrical port;
the third laminectomy lead removably connected to the third cylindrical port;
a silastic sheet;
a first set of electrodes embedded in the silastic sheet;
a second set of electrodes embedded in the silastic sheet;
a first optical director embedded in the silastic sheet adjacent the first set of electrodes;
a second optical director embedded in the silastic sheet adjacent the first set of electrodes and the second set of electrodes;
a third optical director embedded in the silastic sheet adjacent the second set of electrodes;
the first laminectomy lead further comprises a first set of individually addressable electrode lines connected to the first set of electrodes and a first optical transmission fiber connected to the first optical director;
the second laminectomy lead further comprises a second optical transmission fiber connected to the second optical director;
the third laminectomy lead further comprises a second set of individually addressable electrode lines connected to the second set of electrodes and a third optical transmission fiber connected to the third optical director;
wherein the connector body further comprises:
a first electrical contact means for connecting the first set of individually addressable electrode lines to the first set of stimulation signal connectors;
a second electrical contact means for connecting the second set of individually addressable electrode lines to the second set of stimulation signal connectors;
a first optical connection means for connecting the first light detector to the first optical transmission fiber;
a second optical connection means for connecting the light source to the second optical transmission fiber;
a third optical connection means for connecting the second light detector to the third optical transmission fiber;
wherein the IPG further comprises a computer processor programmed to:
activate the light source to emit light through the first optical connection means;

receive first data related to the light from the first light detector through the second optical connection means;
receive second data related to the light from the second light detector through the third optical connection means;
calculate a first set of stimulation data signals based on the first data and the second data;
calculate a second set of stimulation data signals based on the first data and the second data;
send the first set of stimulation data signals to the first set of electrodes through the first electrical contact means; and,
send the second set of stimulation data signals to the second set of electrodes through the second electrical contact means.

\* \* \* \* \*